(12) United States Patent
Takahira

(10) Patent No.: US 9,598,335 B2
(45) Date of Patent: Mar. 21, 2017

(54) METHOD FOR PRODUCING FLUORINE-CONTAINING OLEFIN

(71) Applicant: Asahi Glass Company, Limited, Chiyoda-ku (JP)

(72) Inventor: Yusuke Takahira, Tokyo (JP)

(73) Assignee: ASAHI GLASS COMPANY, LIMITED, Chiyoda-ku (JP)

( * ) Notice: Subject to any disclaimer, the term of this patent is extended or adjusted under 35 U.S.C. 154(b) by 0 days.

(21) Appl. No.: 15/056,288

(22) Filed: Feb. 29, 2016

(65) Prior Publication Data

US 2016/0176791 A1 Jun. 23, 2016

Related U.S. Application Data

(63) Continuation of application No. PCT/JP2014/073065, filed on Sep. 2, 2014.

(30) Foreign Application Priority Data

Sep. 6, 2013 (JP) .................. 2013-185307
Jun. 18, 2014 (JP) .................. 2014-125625

(51) Int. Cl.
*C07F 15/00* (2006.01)
*C07C 17/275* (2006.01)
(Continued)

(52) U.S. Cl.
CPC .......... *C07C 17/275* (2013.01); *C07C 17/272* (2013.01); *C07C 17/37* (2013.01);
(Continued)

(58) Field of Classification Search
CPC ......... C07C 17/35; C07C 41/28; C07C 29/09; C07C 35/00; C07F 15/00
(Continued)

(56) References Cited

U.S. PATENT DOCUMENTS

2003/0100776 A1* 5/2003 Grubbs .................... C07C 6/04
549/513
2007/0155975 A1 7/2007 Grubbs et al.
2014/0288319 A1 9/2014 Grubbs et al.

FOREIGN PATENT DOCUMENTS

WO WO 02/079126 A1 10/2002
WO WO 2009/003085 A1 12/2008

OTHER PUBLICATIONS

International Search report issued Dec. 9, 2014 in PCT/JP2014/073065, filed on Sep. 2, 2014 ( with English Translation).
(Continued)

*Primary Examiner* — Porfirio Nazario Gonzalez
*Assistant Examiner* — Kofi Adzamli
(74) *Attorney, Agent, or Firm* — Oblon, McClelland, Maier & Neustadt, L.L.P.

(57) ABSTRACT

A method for producing at least one compound selected from the group consisting of a compound represented by the following formula (10), a compound represented by the following formula (11), a compound represented by the following formula (12), and a compound represented by the following formula (13), which the method containing reacting a compound represented by the following formula (2) with a compound represented by the following formula (7), in the presence of at least one compound selected from the group consisting of a compound represented by the following formula (1), a compound represented by the following formula (3), a compound represented by the following formula (4), a compound represented by the following formula (8), and a compound represented by the following formula (9).

[Chem. 1]

(Continued)

-continued

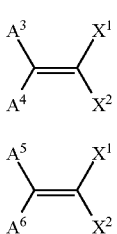

23 Claims, 1 Drawing Sheet

(51) Int. Cl.
C07C 41/30 (2006.01)
C07C 43/17 (2006.01)
C07C 43/176 (2006.01)
C07C 17/37 (2006.01)
C07C 41/22 (2006.01)
C07C 17/272 (2006.01)
C07C 41/18 (2006.01)

(52) U.S. Cl.
CPC .............. *C07C 41/18* (2013.01); *C07C 41/22* (2013.01); *C07C 41/30* (2013.01); *C07C 43/17* (2013.01); *C07C 43/176* (2013.01); *C07F 15/0046* (2013.01); *C07B 2200/09* (2013.01)

(58) Field of Classification Search
USPC .......................................................... 556/22
See application file for complete search history.

(56) References Cited

OTHER PUBLICATIONS

Written Opinion issued Dec. 9, 2014 in PCT/JP2014/073065, filed on Sep. 2, 2014.
Mansa L. MacNaughtan "Ruthenium-Catalyzed Metathesis with Directly Functionalized Olefins", Doctoral Thesis, The University of Michigan, 2009, 59 pages.
Tina M. Trnka et al "Olefin Metathesis with 1,1-Difluoroethylene", Angew. Chem. Int. Ed. vol. 40, No. 18, 2001, 4 pages.
Moo Hong Lim et al. "Synthesis of Novel d-2'-Deoxy-2'-C-difluoromethylene-4'-thiocytidine as a Potential Antitumor Agent", Organic Letters, vol. 4, No. 4, 2002, 3 pages.
Arnab K. Chatterjee et al. "A General Model for Selectivity in Olefins Cross Metathesis", JACS Articles, J. Am. Chem. Soc. vol. 125. No. 37, 2003, 11 pages.
Georgios C. Vougioukalakis et al. "Ruthenium-Based Heterocyclic Carbene-Coordinated Olefin Metathesis Catalysts", Chem Rev. 110, 2010, 42 pages.

* cited by examiner

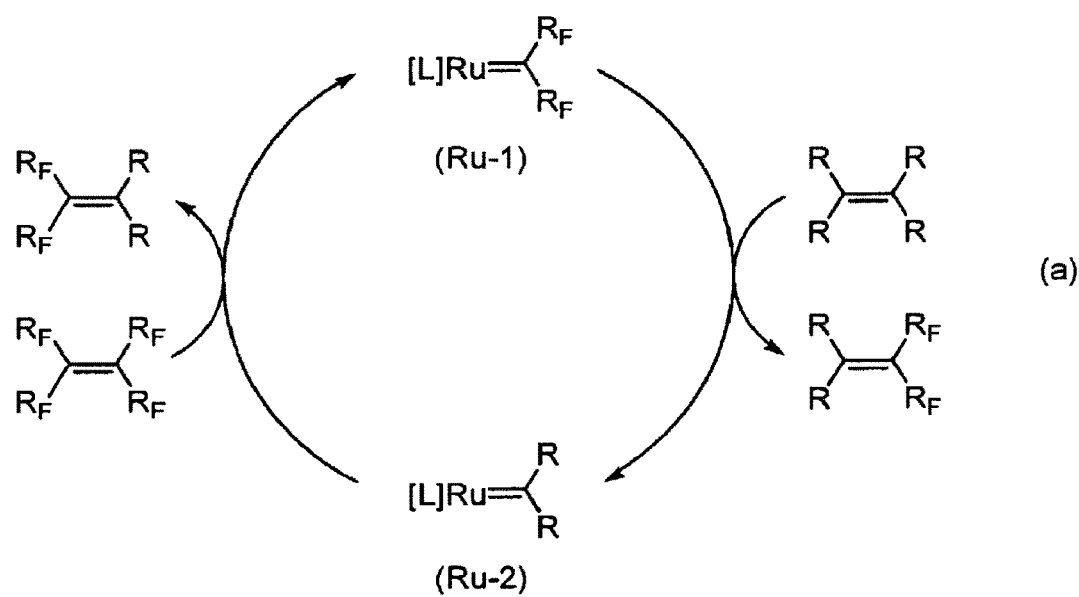

METHOD FOR PRODUCING FLUORINE-CONTAINING OLEFIN

TECHNICAL FIELD

The present invention relates to a novel method for producing a fluorine-containing olefin through olefin metathesis.

BACKGROUND ART

Among olefin compounds where a part or all of hydrogen atoms are substituted with fluorine atoms, that is, fluorine-containing olefins, some industrially-useful compounds are known. For example, 1,1,2-trifluoro-2-substituted olefins such as 1,1,2-trifluorostyrene are compounds useful as organic synthetic building blocks, monomers for polymerization, materials for polymer electrolytes, and the like, and 1,1-difluoro-2,2-disubstituted olefins are compounds useful as materials for medicines such as enzyme inhibitors, for ferroelectric materials and the like. However, no method for simply and efficiently producing these compounds has been established yet. For example, Non-Patent Document 1 reports production of 1,1-difluoro-2,2-disubstituted olefins through Wittig reaction of carbonyl compounds (difluoromethylidenation). However, in the case where the carbonyl compound is a ketone, the yield is low even if an excessive amount (4 to 5 equivalents or more) of Wittig reagent is used, and further, as a phosphorus compound, a carcinogenic hexamethylphosphorous triamide must be used.

Consequently, if other fluorine-containing olefins (e.g., 1,1-difluoro-2,2-disubstituted olefins, etc.) could be simply and efficiently produced from industrially-easily-available fluorine-containing olefins such as tetrafluoroethylene or hexafluoropropylene, the method could be an extremely useful synthesis method as compared with already-existing methods.

On the other hand, olefin metathesis reaction that is a double bond recombination reaction with a metal catalyst (hereinafter this may be simply referred to as "olefin metathesis") is widely utilized as a production method for olefins having various types of substituents. However, electron-deficient olefins having an electron-withdrawing substituent have low reactivity, and therefore use thereof in olefin metathesis is not easy. For example, Non-Patent Document 2 investigates the reactivity of olefins having various substituents and describes that the reactivity of electron-deficient olefins is low. In fact, olefins having a halogen such as a fluorine atom or a chlorine atom are electron-deficient olefins, and therefore there are few reports using them in olefin metathesis. For example, in Non-Patent Document 3, olefin metathesis of a ruthenium complex and vinylidene fluoride (i.e., 1,1-difluoroethylene) is investigated, but the report describes that the expected products, that is, ethylene and tetrafluoroethylene could not be obtained at all. In that manner, use of halogen atom-containing olefins in olefin metathesis is not practicable. Above all, tetrafluoroethylene and hexafluoropropylene are useful compounds from the viewpoint of industrial easy availability and commercialization; however, these are not only extremely electron-deficient olefins but also difficult to handle, and therefore there has been no report relating to use thereof in olefin metathesis.

PRIOR ART DOCUMENTS

Non-Patent Documents

Non-Patent Document 1: Lim, M. H. et al., Org. Lett., 2002, 4, 529-531.

Non-Patent Document 2: Chatterjee, A. K. et al., J. Am. Chem. Soc., 2003, 125, 11360-11370.

Non-Patent Document 3: Trnka, T. et al., Angew. Chem. Int. Ed., 2001, 40, 3441-3444.

SUMMARY OF THE INVENTION

Problems that the Invention is to Solve

Accordingly, an object of the present invention is to provide a method for producing other fluorine-containing olefins such as 1,1-difluoro-2-substituted olefins in a simplified manner and efficiently, from industrially-easily-available fluorine-containing olefins such as tetrafluoroethylene or hexafluoropropylene, through olefin metathesis.

Means for Solving the Problems

As a result of assiduous studies, the present inventors have found that a metal complex containing a ruthenium-carbon double bond and a fluorine-containing olefin such as tetrafluoroethylene (excepting vinylidene fluoride) undergo olefin metathesis under a mild condition to give a difluoromethylidene metal complex and a 1,1-difluoro-2-substituted olefin or the like, and have completed the present invention. In addition, they have found that, when the resultant difluoromethylidene metal complex is subjected to a reaction with an olefin substituted with an organic group, a methylidene metal complex substituted with an organic group regenerates to give a 1,1-difluoro-2-substituted olefin or the like. In particular, they have found that these reactions are catalytic reactions.

That is, the present invention relates to the following (1) to (6).

(1)

A method for producing at least one compound selected from the group consisting of a compound represented by the following formula (3), a compound represented by the following formula (4), a compound represented by the following formula (5), and a compound represented by the following formula (6), which the method containing reacting a compound represented by the following formula (1) with a compound represented by the following formula (2).

[Chem. 1]

(1)

(2)

(3)

(4)

(5)

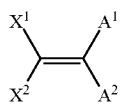

(6)

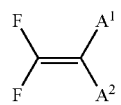

[Chem. 2]

(3)

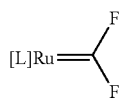

(7)

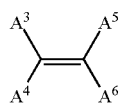

(8)

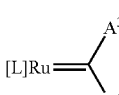

(9)

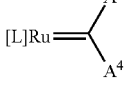

(10)

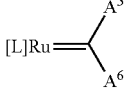

(11)

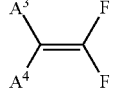

In the formulae, the symbols represent the following meanings.

[L] represents a ligand.

$A^1$ and $A^2$ each independently represent a functional group selected from the group consisting of the following functional group (i), functional group (ii), functional group (iii), and functional group (iv), and these may bond to each other to form a ring. In the case where one of $A^1$ and $A^2$ is a halogen atom, the other is a functional group selected from the group consisting of the functional group (i), the functional group (iii) and the functional group (iv).

$X^1$ and $X^2$ each independently represent a functional group selected from the group consisting of the following functional group (i), the functional group (ii), functional group (v) and functional group (vi), and these may bond to each other to form a ring. In the case where one of $X^1$ and $X^2$ is a hydrogen atom, the other is a functional group selected from the group consisting of the functional group (ii), the functional group (v) and the functional group (vi).

Functional group (i): a hydrogen atom.

Functional group (ii): a halogen atom.

Functional group (iii): a monovalent hydrocarbon group having a carbon number of from 1 to 20.

Functional group (iv): a monovalent hydrocarbon group having a carbon number of from 1 to 20 and containing one or more atoms selected from the group consisting of a halogen atom, an oxygen atom, a nitrogen atom, a sulfur atom, a phosphorus atom, and a silicon atom.

Functional group (v): a functional group selected from the group consisting of an alkyl group having a carbon number of from 1 to 12, an alkoxy group having a carbon number of from 1 to 12, an aryl group having a carbon number of from 5 to 20, an aryloxy group having a carbon number of from 5 to 20, a (per)halogenated alkyl group having a carbon number of from 1 to 12, a (per)halogenated alkoxy group having a carbon number of from 1 to 12, a (per)halogenated aryl group having a carbon number of from 5 to 20, and a (per)halogenated aryloxy group having a carbon number of from 5 to 20.

Functional group (vi): the functional group (v) containing one or more atoms selected from the group consisting of an oxygen atom, a nitrogen atom, a sulfur atom, a phosphorus atom, and a silicon atom.

(2)

A method for producing at least one compound selected from the group consisting of a compound represented by the following formula (8), a compound represented by the following formula (9), a compound represented by the following formula (10), and a compound represented by the following formula (11), which the method containing reacting a compound represented by the following formula (3) with a compound represented by the following formula (7).

In the formulae, the symbols represent the following meanings.

[L] represents a ligand.

$A^3$ to $A^6$ each independently represent a functional group selected from the group consisting of the following functional group (i), functional group (ii), functional group (iii), and functional group (iv). $A^3$ and $A^4$ may bond to each other to form a ring. $A^5$ and $A^6$ may bond to each other to form a ring. In the case where one of $A^3$ and $A^4$ is a halogen atom, the other is a functional group selected from the group consisting of the functional group (i), the functional group (iii) and the functional group (iv). In the case where one of $A^5$ and $A^6$ is a halogen atom, the other is a functional group selected from the group consisting of the functional group (i), the functional group (iii) and the functional group (iv).

Functional group (i): a hydrogen atom.

Functional group (ii): a halogen atom.

Functional group (iii): a monovalent hydrocarbon group having a carbon number of from 1 to 20.

Functional group (iv): a monovalent hydrocarbon group having a carbon number of from 1 to 20 and containing one or more atoms selected from the group consisting of a halogen atom, an oxygen atom, a nitrogen atom, a sulfur atom, a phosphorus atom, and a silicon atom.

(3)

A method for producing at least one compound selected from the group consisting of a compound represented by the following formula (8), a compound represented by the following formula (9), a compound represented by the following formula (12), and a compound represented by the following formula (13), which the method containing reacting a compound represented by the following formula (4) with a compound represented by the following formula (7).

[Chem. 3]

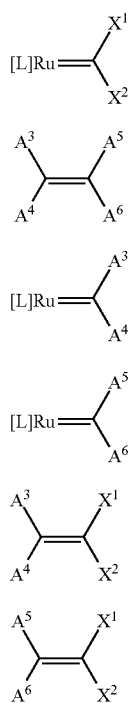

(4)

(7)

(8)

(9)

(12)

(13)

In the formulae, the symbols represent the following meanings.

[L] represents a ligand.

$A^3$ to $A^6$ each independently represent a functional group selected from the group consisting of the following functional group (i), functional group (ii), functional group (iii), and functional group (iv). $A^3$ and $A^4$ may bond to each other to form a ring. $A^5$ and $A^6$ may bond to each other to form a ring. In the case where one of $A^3$ and $A^4$ is a halogen atom, the other is a functional group selected from the group consisting of the functional group (i), the functional group (iii) and the functional group (iv). In the case where one of $A^5$ and $A^6$ is a halogen atom, the other is a functional group selected from the group consisting of the functional group (i), the functional group (iii) and the functional group (iv).

$X^1$ and $X^2$ each independently represent a functional group selected from the group consisting of the following functional group (i), functional group (ii), functional group (v), and functional group (vi), and these may bond to each other to form a ring. In the case where one of $X^1$ and $X^2$ is a hydrogen atom, the other is a functional group selected from the group consisting of the functional group (ii), the functional group (v) and the functional group (vi).

Functional group (i): a hydrogen atom.

Functional group (ii): a halogen atom.

Functional group (iii): a monovalent hydrocarbon group having a carbon number of from 1 to 20.

Functional group (iv): a monovalent hydrocarbon group having a carbon number of from 1 to 20 and containing one or more atoms selected from the group consisting of a halogen atom, an oxygen atom, a nitrogen atom, a sulfur atom, a phosphorus atom, and a silicon atom.

Functional group (v): a functional group selected from the group consisting of an alkyl group having a carbon number of from 1 to 12, an alkoxy group having a carbon number of from 1 to 12, an aryl group having a carbon number of from 5 to 20, an aryloxy group having a carbon number of from 5 to 20, a (per)halogenated alkyl group having a carbon number of from 1 to 12, a (per)halogenated alkoxy group having a carbon number of from 1 to 12, a (per)halogenated aryl group having a carbon number of from 5 to 20, and a (per)halogenated aryloxy group having a carbon number of from 5 to 20.

Functional group (vi): the functional group (v) containing one or more atoms selected from the group consisting of an oxygen atom, a nitrogen atom, a sulfur atom, a phosphorus atom, and a silicon atom.

(4) A method for producing at least one compound selected from the group consisting of a compound represented by the following formula (10), a compound represented by the following formula (11), a compound represented by the following formula (12), and a compound represented by the following formula (13), which the method containing:

reacting at least one of a compound represented by the following formula (3) and a compound represented by the following formula (4), with a compound represented by the following formula (7) to give at least one of a compound represented by the following formula (8) and a compound represented by the following formula (9), and reacting at least one of the compound represented by the formula (8) and the compound represented by the formula (9), with a compound represented by the following formula (2).

[Chem. 4]

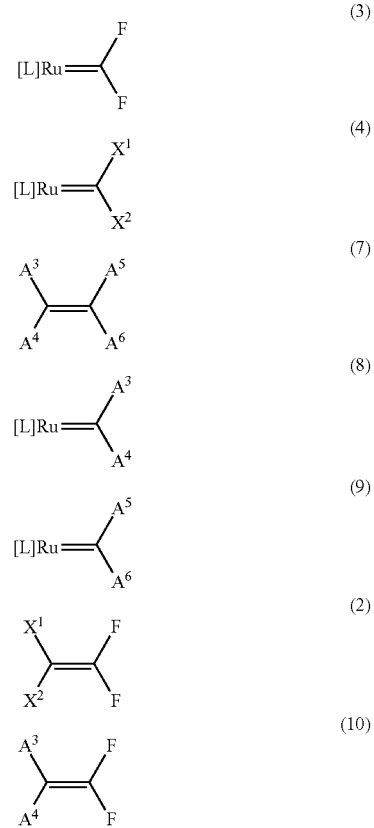

(3)

(4)

(7)

(8)

(9)

(2)

(10)

-continued

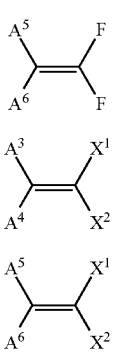

In the formulae, the symbols represent the following meanings.

[L] represents a ligand.

$A^3$ to $A^6$ each independently represent a functional group selected from the group consisting of the following functional group (i), functional group (ii), functional group (iii), and functional group (iv). $A^3$ and $A^4$ may bond to each other to form a ring. $A^5$ and $A^6$ may bond to each other to form a ring. In the case where one of $A^3$ and $A^4$ is a halogen atom, the other is a functional group selected from the group consisting of the functional group (i), the functional group (iii) and the functional group (iv). In the case where one of $A^5$ and $A^6$ is a halogen atom, the other is a functional group selected from the group consisting of the functional group (i), the functional group (iii) and the functional group (iv).

$X^1$ and $X^2$ each independently represent a functional group selected from the group consisting of the following functional group (i), functional group (ii), functional group (v), and functional group (vi), these may bond to each other to form a ring. In the case where one of $X^1$ and $X^2$ is a hydrogen atom, the other is a functional group selected from the group consisting of the functional group (ii), the functional group (v) and the functional group (vi).

Functional group (i): a hydrogen atom.

Functional group (ii): a halogen atom.

Functional group (iii): a monovalent hydrocarbon group having a carbon number of from 1 to 20.

Functional group (iv): a monovalent hydrocarbon group having a carbon number of from 1 to 20 and containing one or more atoms selected from the group consisting of a halogen atom, an oxygen atom, a nitrogen atom, a sulfur atom, a phosphorus atom, and a silicon atom.

Functional group (v): a functional group selected from the group consisting of an alkyl group having a carbon number of from 1 to 12, an alkoxy group having a carbon number of from 1 to 12, an aryl group having a carbon number of from 5 to 20, an aryloxy group having a carbon number of from 5 to 20, a (per)halogenated alkyl group having a carbon number of from 1 to 12, a (per)halogenated alkoxy group having a carbon number of from 1 to 12, a (per)halogenated aryl group having a carbon number of from 5 to 20, and a (per)halogenated aryloxy group having a carbon number of from 5 to 20.

Functional group (vi): the functional group (v) containing one or more atoms selected from the group consisting of an oxygen atom, a nitrogen atom, a sulfur atom, a phosphorus atom, and a silicon atom.

(5) A method for producing at least one compound selected from the group consisting of a compound represented by the following formula (10), a compound represented by the following formula (11), a compound represented by the following formula (12), and a compound represented by the following formula (13), which the method containing:

reacting at least one of a compound represented by the following formula (8) and a compound represented by the following formula (9), with a compound represented by the following formula (2) to give at least one of a compound represented by the following formula (3) and a compound represented by the following formula (4), and reacting at least one of the compound represented by the formula (3) and the compound represented by the formula (4), with a compound represented by the following formula (7).

[Chem. 5]

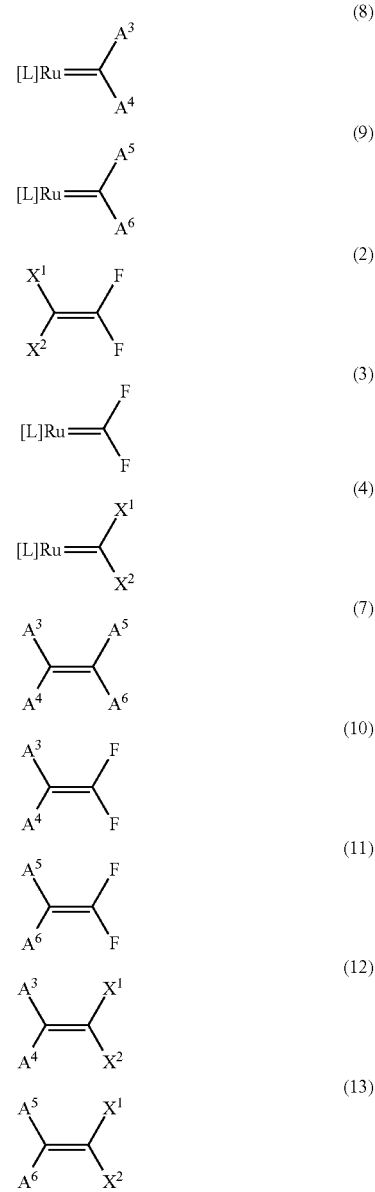

In the formulae, the symbols represent the following meanings.

[L] represents a ligand.

$A^3$ to $A^6$ each independently represent a functional group selected from the group consisting of the following functional group (i), functional group (ii), functional group (iii), and functional group (iv). $A^3$ and $A^4$ may bond to each other to form a ring. $A^5$ and $A^6$ may bond to each other to form a ring. In the case where one of $A^3$ and $A^4$ is a halogen atom, the other is a functional group selected from the group consisting of the functional group (i), the functional group (iii) and the functional group (iv). In the case where one of $A^5$ and $A^6$ is a halogen atom, the other is a functional group selected from the group consisting of the functional group (i), the functional group (iii) and the functional group (iv).

$X^1$ and $X^2$ each independently represent a functional group selected from the group consisting of the following functional group (i), functional group (ii), functional group (v), and functional group (vi), these may bond to each other to form a ring. In the case where one of $X^1$ and $X^2$ is a hydrogen atom, the other is a functional group selected from the group consisting of the functional group (ii), the functional group (v) and the functional group (vi).

Functional group (i): a hydrogen atom.
Functional group (ii): a halogen atom.
Functional group (iii): a monovalent hydrocarbon group having a carbon number of from 1 to 20.
Functional group (iv): a monovalent hydrocarbon group having a carbon number of from 1 to 20 and containing one or more atoms selected from the group consisting of a halogen atom, an oxygen atom, a nitrogen atom, a sulfur atom, a phosphorus atom, and a silicon atom.
Functional group (v): a functional group selected from the group consisting of an alkyl group having a carbon number of from 1 to 12, an alkoxy group having a carbon number of from 1 to 12, an aryl group having a carbon number of from 5 to 20, an aryloxy group having a carbon number of from 5 to 20, a (per)halogenated alkyl group having a carbon number of from 1 to 12, a (per)halogenated alkoxy group having a carbon number of from 1 to 12, a (per)halogenated aryl group having a carbon number of from 5 to 20, and a (per)halogenated aryloxy group having a carbon number of from 5 to 20.
Functional group (vi): the functional group (v) containing one or more atoms selected from the group consisting of an oxygen atom, a nitrogen atom, a sulfur atom, a phosphorus atom, and a silicon atom.

(6) A method for producing at least one compound selected from the group consisting of a compound represented by the following formula (10), a compound represented by the following formula (11), a compound represented by the following formula (12), and a compound represented by the following formula (13), which the method containing reacting a compound represented by the following formula (2) with a compound represented by the following formula (7), in the presence of at least one compound selected from the group consisting of a compound represented by the following formula (1), a compound represented by the following formula (3), a compound represented by the following formula (4), a compound represented by the following formula (8), and a compound represented by the following formula (9).

[Chem. 6]

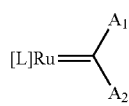

(1)

-continued

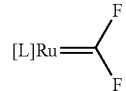

(3)

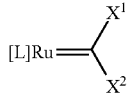

(4)

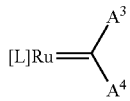

(8)

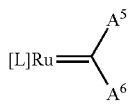

(9)

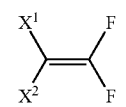

(2)

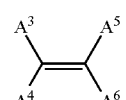

(7)

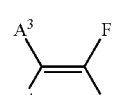

(10)

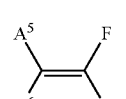

(11)

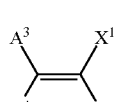

(12)

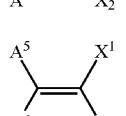

(13)

In the formulae, the symbols represent the following meanings.

[L] represents a ligand.

$A^1$ to $A^6$ each independently represent a functional group selected from the group consisting of the following functional group (i), functional group (ii), functional group (iii), and functional group (iv). $A^1$ and $A^2$ may bond to each other to form a ring. $A^3$ and $A^4$ may bond to each other to form a ring. $A^5$ and $A^6$ may bond to each other to form a ring. In the case where one of $A^1$ and $A^2$ is a halogen atom, the other is a functional group selected from the group consisting of the functional group (i), the functional group (iii) and the functional group (iv). In the case where one of $A^3$ and $A^4$ is a halogen atom, the other is a functional group selected from the group consisting of the functional group (i), the functional group (iii) and the functional group (iv). In the case where one of $A^5$ and $A^6$ is a halogen atom, the other is a functional group selected from the group consisting of the functional group (i), the functional group (iii) and the functional group (iv).

X¹ and X² each independently represent a functional group selected from the group consisting of the following functional group (i), functional group (ii), functional group (v) and functional group (vi), these may bond to each other to form a ring. In the case where one of X¹ and X² is a hydrogen atom, the other is a functional group selected from the group consisting of the functional group (ii), the functional group (v) and the functional group (vi).

Functional group (i): a hydrogen atom.
Functional group (ii): a halogen atom.
Functional group (iii): a monovalent hydrocarbon group having a carbon number of from 1 to 20.
Functional group (iv): a monovalent hydrocarbon group having a carbon number of from 1 to 20 and containing one or more atoms selected from the group consisting of a halogen atom, an oxygen atom, a nitrogen atom, a sulfur atom, a phosphorus atom, and a silicon atom.
Functional group (v): a functional group selected from the group consisting of an alkyl group having a carbon number of from 1 to 12, an alkoxy group having a carbon number of from 1 to 12, an aryl group having a carbon number of from 5 to 20, an aryloxy group having a carbon number of from 5 to 20, a (per)halogenated alkyl group having a carbon number of from 1 to 12, a (per)halogenated alkoxy group having a carbon number of from 1 to 12, a (per)halogenated aryl group having a carbon number of from 5 to 20, and a (per)halogenated aryloxy group having a carbon number of from 5 to 20.
Functional group (vi): the functional group (v) containing one or more atoms selected from the group consisting of an oxygen atom, a nitrogen atom, a sulfur atom, a phosphorus atom, and a silicon atom.

Advantageous Effects of the Invention

According to the production method for fluorine-containing olefins of the present invention, other fluorine-containing olefins such as 1,1-difluoro-2-substituted olefins can be simply and efficiently produced from industrially-easily-available fluorine-containing olefins such as tetrafluoroethylene or hexafluoropropylene, through olefin metathesis.

BRIEF DESCRIPTION OF DRAWINGS

FIG. 1 is a scheme showing one example of the production method for fluorine-containing olefins through olefin metathesis of the present invention.

MODES FOR CARRYING OUT THE INVENTION

The present invention is described in detail hereinunder, but the present invention is not limited to the following embodiments. Within a range not overstepping the scope thereof, the present invention may be carried out in any modifications. In addition, the present invention relates to olefin metathesis with a metal catalyst, and description of general features common to those in conventional techniques may be omitted hereunder.

In this description, "a compound represented by a formula (X)" may be simply referred to as "a compound (X)".

Also in this description, the wording "1,1-difluoro-2-substituted olefins and the like" encompasses both 1,1-difluoro-2-substituted olefins and 1,1-difluoro-2,2-disubstituted olefins. The "1,1-difluoro-2-substituted olefin" means an olefin in which two fluorine atoms bond to one carbon atom of the double bond and one hydrogen atom and one organic group bond to the other carbon atom. The "1,1-difluoro-2,2-di-substituted olefin" means an olefin in which two fluorine atoms bond to one carbon atom of the double bond and the same two or different organic groups bond to the other carbon atoms.

The perhalogenated alkyl group means a group in which all hydrogen atoms of the alkyl group are substituted with halogen atoms. The perhalogenated alkoxy group means a group in which all hydrogen atoms of the alkoxy group are substituted with halogen atoms. The same shall apply to the perhalogenated alkoxy group and the perhalogenated aryl group.

The (per)halogenated alkyl group is used as a generic term including both a halogenated alkyl group and a perhalogenated alkyl group. That is, the group is an alkyl group having one or more halogen atoms. The same shall apply to the (per)halogenated alkoxy group, the (per)halogenated aryl group and the (per)halogenated aryloxy group.

The aryl group means a monovalent group corresponding to a residue derived by removing one hydrogen atom bonding to any one carbon atom in the carbon atoms forming an aromatic ring in an aromatic compound, and is used as a generic term including an aryl group derived from a carbon-cyclic compound and a heteroaryl group derived from a heterocyclic compound.

The carbon number of the hydrocarbon group means the total number of the carbon atoms contained in the whole of a hydrocarbon group, and in the case where the group does not have a substituent, the carbon number means the number of the carbon atoms forming the hydrocarbon group skeleton, while in the case where the group has a substituent, the carbon number means the sum of the number of the carbon atoms forming the hydrocarbon group skeleton and the number of the carbon atoms in the substituent.

<Reaction Mechanism>

The present invention relates to a production method for fluorine-containing olefins through olefin metathesis, and is, for example, characterized by including an intermediate (Ru-1) and an intermediate (Ru-2) as a part of the reaction mechanism thereof, as shown by the following scheme (a).

[Chem. 7]

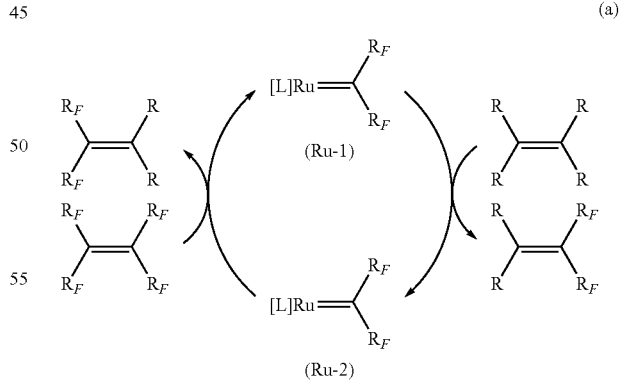

(a)

In the above-mentioned scheme (a), [L] is a ligand, plural R's each are independently an organic group, and plural $R_F$'s each are independently a fluorine atom or an organic group having at least one fluorine atom in the group.

Olefin metathesis reaction is reversible. That is, the scheme (a) includes a reversed reaction (reaction represented by an arrow in the reversed direction). However, detailed description of this point is omitted. Furthermore, the olefin to be produced may have geometric isomers. However, the detailed description of this point is omitted because it strongly depends on the individual reactions.

The above-mentioned scheme (a) is specifically described with respect to the following schemes (b) to (k).

The present invention is, as shown by the following scheme (b), characterized in that a compound (2) is reacted with a compound (7) in the presence of a compound (1) to produce at least any one of a compound (10) and a compound (11).

In the above-mentioned scheme, the compound (1) is described as a representative example of a ruthenium-carbene complex. The ruthenium-carbene complex may also be a compound (3), a compound (4), a compound (8), or a compound (9) to be mentioned below, and hereinafter the same shall apply to the ruthenium carbene complexes.

[Chem. 8]

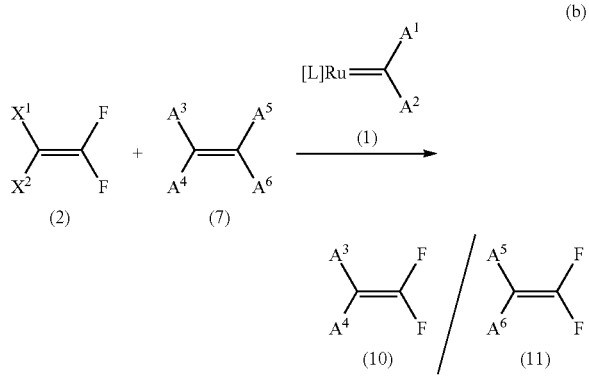

(b)

In this description, the symbols in the formulae have the following meanings.

[L] represents a ligand.

$A^1$ to $A^6$ each independently represent a functional group selected from the group consisting of the following functional group (i), functional group (ii), functional group (iii), and functional group (iv). $A^1$ and $A^2$ may bond to each other to form a ring. $A^3$ and $A^4$ may bond to each other to form a ring. $A^5$ and $A^6$ may bond to each other to form a ring. In the case where one of $A^1$ and $A^2$ is a halogen atom, the other is a functional group selected from the group consisting of the functional group (i), the functional group (iii) and the functional group (iv). In the case where one of $A^3$ and $A^4$ is a halogen atom, the other is a functional group selected from the group consisting of the functional group (i), the functional group (iii) and the functional group (iv). In the case where one of $A^5$ and $A^6$ is a halogen atom, the other is a functional group selected from the group consisting of the functional group (i), the functional group (iii) and the functional group (iv).

$X^1$ and $X^2$ each independently represent a functional group selected from the group consisting of the following functional group (i), functional group (ii), functional group (v), and functional group (vi), and these may bond to each other to form a ring. In the case where one of $X^1$ and $X^2$ is a hydrogen atom, the other is a functional group selected from the group consisting of the functional group (ii), the functional group (v) and the functional group (vi).

The functional group (i) to the functional group (vii) have the following meanings.

Functional group (i): a hydrogen atom.

Functional group (ii): a halogen atom.

Functional group (iii): a monovalent hydrocarbon group having a carbon number of from 1 to 20.

Functional group (iv): a monovalent hydrocarbon group having a carbon number of from 1 to 20 and containing one or more atoms selected from the group consisting of a halogen atom, an oxygen atom, a nitrogen atom, a sulfur atom, a phosphorus atom, and a silicon atom.

Functional group (v): a functional group selected from the group consisting of an alkyl group having a carbon number of from 1 to 12, an alkoxy group having a carbon number of from 1 to 12, an aryl group having a carbon number of from 5 to 20, an aryloxy group having a carbon number of from 5 to 20, a (per)halogenated alkyl group having a carbon number of from 1 to 12, a (per)halogenated alkoxy group having a carbon number of from 1 to 12, a (per)halogenated aryl group having a carbon number of from 5 to 20, and a (per)halogenated aryloxy group having a carbon number of from 5 to 20.

Functional group (vi): the functional group (v) containing one or more atoms selected from the group consisting of an oxygen atom, a nitrogen atom, a sulfur atom, a phosphorus atom, and a silicon atom.

Further, the present invention is characterized by producing at least any one of a compound (12) and a compound (13) by reacting a compound (2) and a compound (7) in the presence of a compound (1), as shown by the following scheme (c).

[Chem. 9]

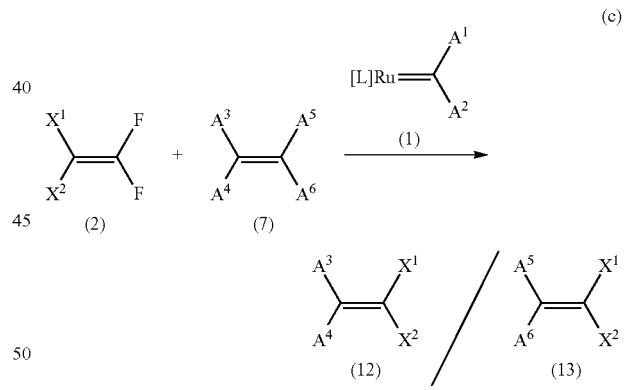

(c)

That is, as shown by the scheme (b) and/or the scheme (c), the compound (2) and the compound (7) produce at least one of the compound (10) to the compound (13) through olefin metathesis using the compound (1) as a catalyst.

In the reaction process, the compound (2) and the compound (1) serving as a catalyst produce, as an intermediate compound, at least any one of the compound (3) and the compound (4) and/or at least any one of the compound (5) and the compound (6), through olefin metathesis as shown by the following scheme (d) and/or the scheme (e).

That is, olefin metathesis of the compound (1) and the compound (2) produces at least one of the compound (3) to the compound (6).

[Chem. 10]

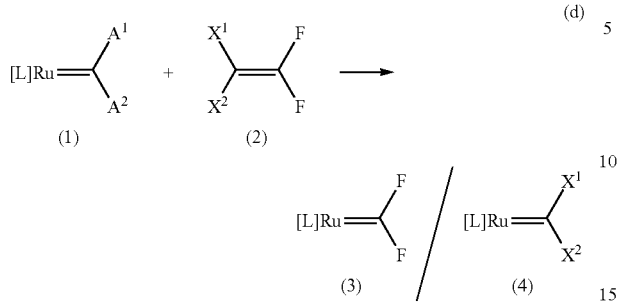

[Chem. 11]

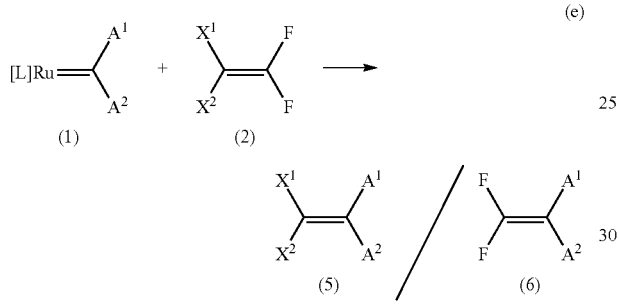

The resultant compound (3) or compound (4) each produces at least one of the compound (10) and the compound (11) or at least one of the compound (12) and the compound (13) through olefin metathesis with the compound (7), as shown by the following scheme (f) or scheme (g).

[Chem. 12]

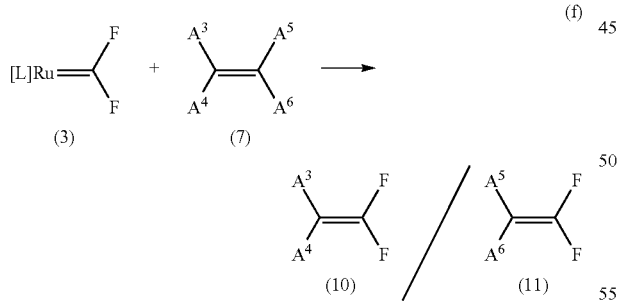

[Chem. 13]

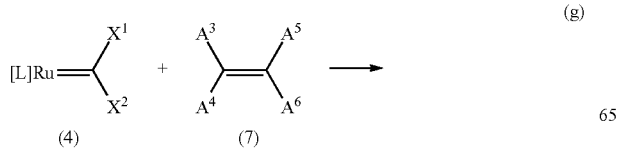

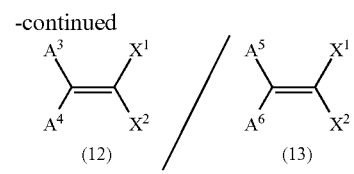

That is, it is considered that, in the reaction represented by the scheme (b) and the scheme (c), strictly, at least two steps of reaction of the scheme (d) and the scheme (e) as well as the scheme (f) and the scheme (g) would occur.

In each of the above scheme (f) and scheme (g), at least one of the compound (3) and the compound (4) gives at least any one compound represented by the following formula (8) and formula (9) as a ruthenium complex, through olefin metathesis with the compound (7) as shown by the following scheme (h).

[Chem. 14]

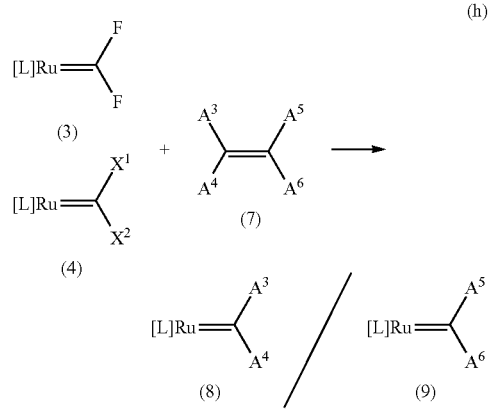

That is, olefin metathesis of the compound (3) with the compound (7) gives at least one compound selected from the group consisting of the compound (8) to the compound (11).

In addition, olefin metathesis of the compound (4) with the compound (7) gives at least one compound selected from the group consisting of the compound (8), the compound (9), the compound (12), and the compound (13).

In the scheme (d) and the scheme (e), it is considered that the reaction of the compound (1) with the compound (2) gives the compounds (3) to (6), via intermediates represented by the following formula (14) and formula (15). Similarly, it is considered that, in the scheme (f), via intermediates represented by the following formula (16) and/or formula (17), and in the scheme (g), via intermediates represented by the following formula (18) and/or formula (19), the compound (10) to the compound (13) would be produced. The compounds (10) to (13) include geometric isomers, and according to the present invention, both geometric isomers can be produced.

[Chem. 15]

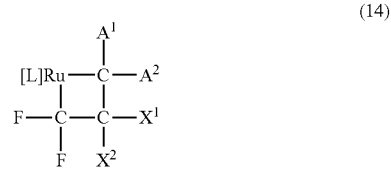

[Chem. 16]

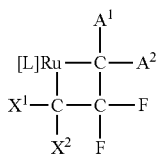
(15)

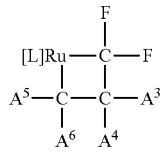
(16)

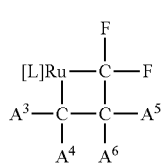
(17)

[Chem. 17]

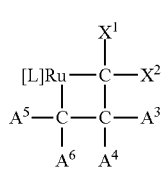
(18)

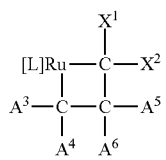
(19)

The compound (8) or the compound (9) obtained in the scheme (f) and the scheme (g) gives at least any one of the compound (3) and the compound (4) through olefin metathesis with the compound (2), as shown by the following scheme (i).

[Chem. 18]

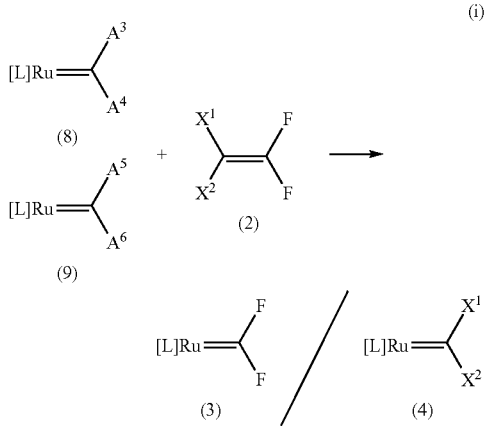

Also, the compound (8) or the compound (9) gives at least any one of the compound (10) and the compound (12) or at least any one of the compound (11) and the compound (13), through olefin metathesis with the compound (2) as shown by the following scheme (j) or scheme (k).

[Chem. 19]

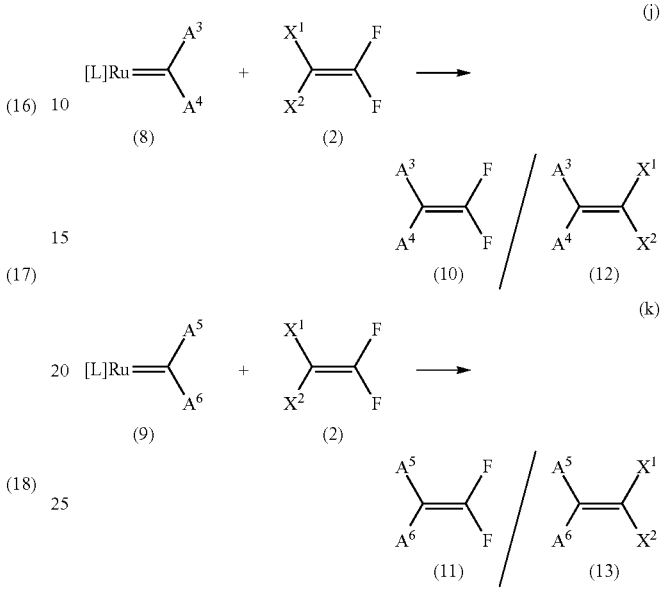

The schemes (h), (j) and (k) are summarized. Olefin metathesis of at least any one of the compound (3) and the compound (4) with the compound (7) gives at least one of the compound (8) and the compound (9); and olefin metathesis of at least one of the compound (8) and the compound (9) with the compound (2) gives at least one compound selected from the group consisting of the compound (10) to the compound (13).

The schemes (i), (f) and (g) are summarized. Olefin metathesis of at least any one of the compound (8) and the compound (9) with the compound (2) gives at least one of the compound (3) and the compound (4); and olefin metathesis of at least one of the compound (3) and the compound (4) with the compound (7) gives at least one compound selected from the group consisting of the compound (10) to the compound (13).

The schemes (b), (c) and (f) to (k) are summarized. Olefin metathesis of the compound (2) with the compound (7) with a catalyst of at least one ruthenium complex selected from the group consisting of the compound (1), the compound (3), the compound (4), the compound (8), and the compound (9) gives at least one compound selected from the group consisting of the compound (10) to the compound (13).

In the schemes (b) and (c), the compound (1) may react with the compound (7) to give at least one of the compound (8) and the compound (9), leading to the progress of the reaction of the schemes (i), (j), (k).

Accordingly, the olefin metathesis in the present invention may be expressed as a series of cycle reaction. The cycle reaction may be represented, for example, as in the following scheme (I). In the following scheme (I), R represents an organic group, including, for example, an alkyl group such as a butyl group. The following scheme (I) includes upper and lower two cycles. Of the two cycles, one cycle alone may occur or both the two cycles may competitively occur, depending on the combination of the olefin compounds to be supplied in the system.

[Chem. 20]

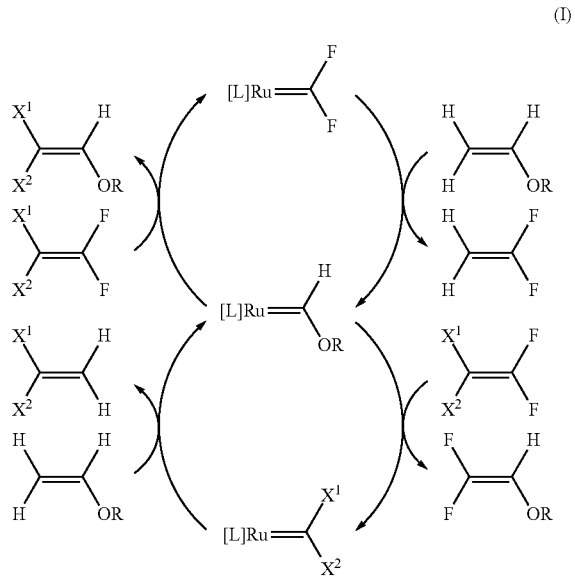

(I)

Here, a preferred embodiment of the series of olefin metathesis is shown by the following scheme (II). In the scheme, nominal formation of the compound in parenthesis "( )" could be anticipated, but in experiments, the compound did not form or formed little and could hardly be detected. That is, the parenthesized compound is not the main product in each elementary reaction. This may be considered to be derived from the difference in the stability of the two types of ruthenium-carbene complexes. That is, in the scheme (II), this may be considered to be derived from the difference in the stability between the compound (8-1) and the compound (9-1). In other words, the compound (9-1) is more stable than the compound (8-1), and therefore the amount of the compound to be formed as a result of reaction would differ.

Also in the scheme (II), it is considered that the matter whether the catalytic reaction cycle shown on the right side could go on favorably would depend on the difference in the stability between the two types of the ruthenium-carbene complexes that are considered to be important intermediates in the reaction. That is, in the scheme (II), it is considered that, when the difference in the stability between the compound (3-1)/(4-1) and the compound (9-1) is smaller, the catalytic reaction cycle could go on more favorably. Consequently, it is considered that, as shown by the compound (9-1), the reaction system to produce a compound in which a hetero atom (atom excepting carbon atom or hydrogen atom) bonds to the carbon atom of the ruthenium-carbene complex (e.g., Fischer-type carbene complex) would be preferable to favorably progress the catalytic reaction cycle.

[Chem. 21]

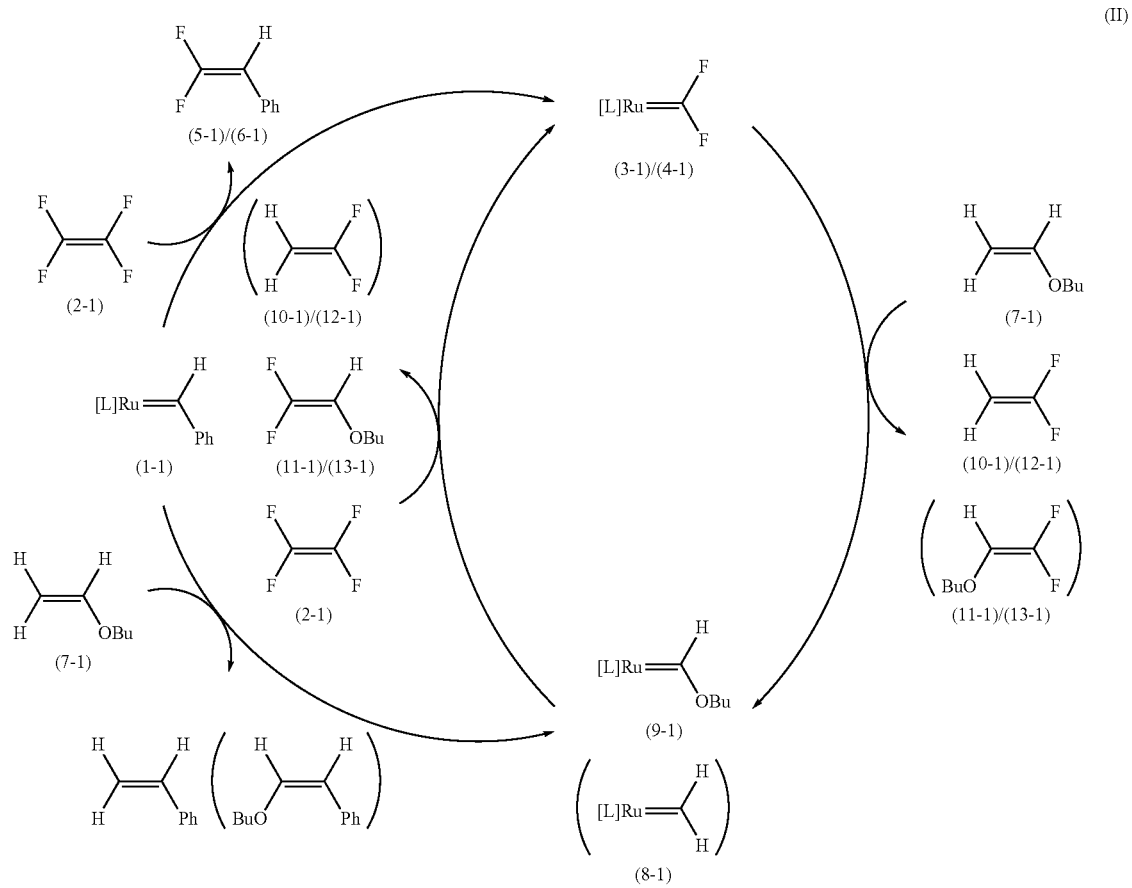

(II)

In the scheme (II), [L] in the compound (1-1), the compound (3-1), the compound (4-1), the compound (8-1), and the compound (9-1) represents a ligand, and the details of each compound are as follows.

Compound (1-1): compound where, in compound (1), $A^1$ is a hydrogen atom and $A^2$ is a phenyl group (Ph).

Compound (2-1): compound where, in compound (2), $X^1$ and $X^2$ are both fluorine atoms.

Compound (4-1): compound where, in compound (4), $X^1$ and $X^2$ are both fluorine atoms.

Compound (5-1): compound where, in compound (5), $A^1$ is a hydrogen atom, $A^2$ is a phenyl group (Ph), and $X^1$ and $X^2$ are both fluorine atoms.

Compound (6-1): compound where, in compound (6), $A^1$ is a hydrogen atom and $A^2$ is a phenyl group (Ph).

Compound (7-1): compound where, in compound (7), $A^3$ to $A^5$ are hydrogen atoms, and $A^6$ is a butoxy group (OBu) (in this, Bu is $(CH_2)_3CH_3$).

Compound (8-1): compound where, in compound (8), $A^3$ and $A^4$ are both hydrogen atoms.

Compound (9-1): compound where, in compound (9), $A^5$ is a hydrogen atom, and $A^6$ is a butoxy group (OBu).

Compound (10-1): compound where, in compound (10), $A^3$ and $A^4$ are both hydrogen atoms.

Compound (11-1): compound where, in compound (11), $A^5$ is a hydrogen atom, and $A^6$ is a butoxy group (OBu).

Compound (12-1): compound where, in compound (12), $A^3$ and $A^4$ are both hydrogen atoms, and $X^1$ and $X^2$ are both fluorine atoms.

Compound (13-1): compound where, in compound (13), $A^5$ is a hydrogen atom, $A^6$ is a butoxy group (OBu), and $X^1$ and $X^2$ are both fluorine atoms.

<Compound (1)>

The compound (1) serves as a catalyst in the production method of the present invention, and means both one charged as a reagent and one formed during the reaction (catalytically active species). Here, as the compound (1), known are both one that comes to exhibit catalytic activity through dissociation of some ligands under the reaction condition, and one that exhibits catalytic activity with no dissociation of ligands, and any of these is employable in the present invention with no limitation. In general, olefin metathesis proceeds with repeating olefin coordination and dissociation with and from catalyst, and therefore during reaction, it is not always definite how many ligands except olefin could coordinate on the catalyst. Consequently, in this description, [L] does not specifically define the number and the type of ligand.

$A^1$ and $A^2$ in the compound (1) each independently represent a functional group selected from the group consisting of the functional group (i), the functional group (ii), the functional group (iii), and the functional group (iv). $A^1$ and $A^2$ may bond to each other to form a ring. In the case where one of $A^1$ and $A^2$ is a halogen atom, the other is a functional group selected from the group consisting of the functional group (i), the functional group (iii) and the functional group (iv). That is $A^1$ and $A^2$ in the compound (1) each are independently a hydrogen atom, a halogen atom, a monovalent hydrocarbon group having a carbon number of from 1 to 20, or a monovalent hydrocarbon group having a carbon number of from 1 to 20 and containing one or more atoms selected from the group consisting of an oxygen atom, a nitrogen atom, a sulfur atom, a phosphorus atom, and a silicon atom, and these may bond to each other to form a ring. However, the compound (1) excludes a case where both $A^1$ and $A^2$ are halogen atoms.

The halogen atom includes a fluorine atom, a chlorine atom, a bromine atom, and an iodine atom. From the viewpoint of easily-availability, preferred are a fluorine atom and a chlorine atom.

The monovalent hydrocarbon group having a carbon number of from 1 to 20 is preferably an alkyl group having a carbon number of from 1 to 20 or an aryl group having a carbon number of from 5 to 20, and may be linear, branched or cyclic.

Preferred examples of the monovalent hydrocarbon group having a carbon number of from 1 to 20 and containing one or more atoms selected from the group consisting of a halogen atom, an oxygen atom, a nitrogen atom, a sulfur atom, a phosphorus atom, and a silicon atom include an alkyl group having a carbon number of from 1 to 20 or alkoxy group having a carbon number of from 1 to 20 which contain the aforementioned atom, and an aryl group having a carbon number of from 5 to 20 or aryloxy group having a carbon number of from 5 to 20 which contain the aforementioned atom. The monovalent hydrocarbon group may be linear, branched or cyclic. In these preferred groups, a halogen atom may bond to a part of the carbon atoms. That is, for example, the group may be a (per)fluoroalkyl group or a (per)fluoroalkoxy group. Also these preferred groups may have an etheric oxygen atom between the carbon atom and the carbon atom. Also these preferred groups may have a substituent containing one or more atoms selected from the group consisting of a halogen atom, an oxygen atom, a nitrogen atom, a sulfur atom, a phosphorus atom, and a silicon atom. Examples of the substituent include a hydroxyl group, an amino group, an imino group, a nitrile group, an amide group (a carbonylamino group), a carbamate group (an oxycarbonylamino group), a nitro group, a carboxyl group, an ester group (an acyloxy group or an alkoxycarbonyl group), a thioether group, silyl group, and the like. These groups may be further substituted with an alkyl group or an aryl group. For example, the amino group ($-NH_2$) may be a monoalkylamino group ($-NHR$), a monoaryl amino group ($-NHAr$), a dialkylamino group ($-NR_2$), or a diarylamino group ($-NAr_2$).

Preferred examples of the compound (1) having a combination of these $A^1$ and $A^2$ include ones represented by the following formulae, from the viewpoint of the availability thereof.

[Chem. 22]

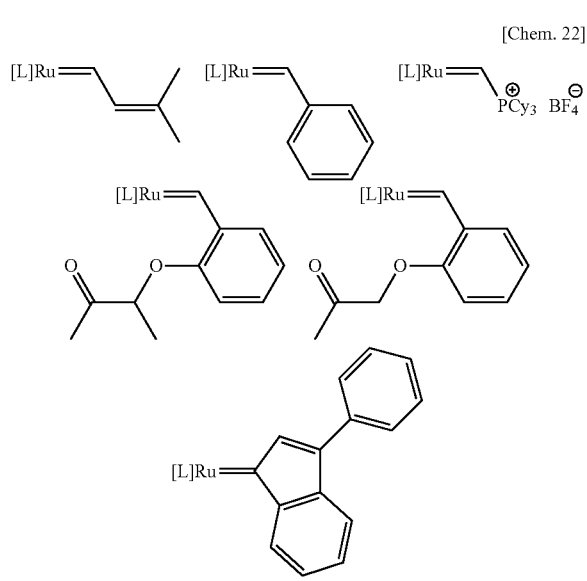

-continued

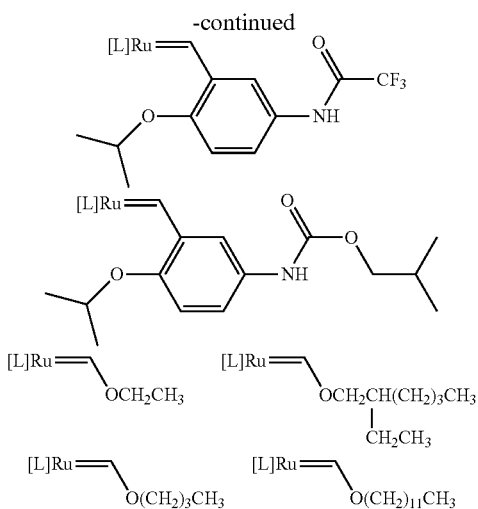

Specifically, the compound (1) can be represented by the following formula (1-A). The ligand [L] in the formula (1) is represented by $L^1$, $L^2$, $L^3$, $Z^1$, and $Z^2$ in the formula (1-A). The positions of $L^1$, $L^2$, $L^3$, $Z^1$, and $Z^2$ are not specifically defined, and these may be alternated to each other in the formula (1-A). That is, for example, $Z^1$ and $Z^2$ may be at the trans-position or at the cis-position.

[Chem. 23]

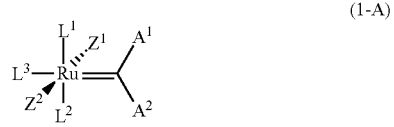

(1-A)

In the formula (1-A), $L^1$, $L^2$ and $L^3$ each independently represent a ligand that has a neutral charge when dissociated from the central metal (a neutral electron-donating ligand). Concretely, there are mentioned a carbonyl group, amines, imines, pyridines, ethers, nitriles, esters, phosphines, thioethers, sulfoxides, sulfones, aromatic compounds, olefins, isocyanides, thiocyanates, hetero atom-containing carbene compounds, and the like. Of those, preferred are phosphines, pyridines and hetero atom-containing carbene compounds, and more preferred are trialkyl phosphines and N-heterocyclic carbene compounds.

However, depending on the combination of the above-mentioned ligands, all ligands could not coordinate with the central metal owing to steric factors and/or electronic factors, and as a result, some coordination positions may be vacant sites. For example, $L^1$, $L^2$ and $L^3$ include the following combinations. $L^1$: a hetero atom-containing carbene compound, $L^2$: a phosphine, $L^3$: vacant (vacant coordination site). $L^1$: a hetero atom-containing carbene compound, $L^2$: a pyridine, $L^3$: a pyridine.

In the formula (1-A), $Z^1$ and $Z^2$ each are independently a ligand that has a negative charge when dissociated from the central metal (anionic ligand). Concretely, there are mentioned a halogen atom, a hydrogen atom, a substituted diketonate group, a substituted cyclopentadienyl group, an alkyl group having a carbon number of from 1 to 20, an aryl group having a carbon number of from 5 to 20, a substituted alkoxy group having a carbon number of from 1 to 20, a substituted aryloxy group having a carbon number of from 5 to 20, a substituted carboxylate group having a carbon number of from 1 to 20, a substituted arylcarboxylate group having a carbon number of from 6 to 20, a substituted alkylthiolate group having a carbon number of from 1 to 20, a substituted arylthiolate group having a carbon number of from 6 to 20, a nitrate group, and the like. Above all, preferred is a halogen atom, and more preferred is a chlorine atom.

In the formula (1-A), $A^1$ and $A^2$ are the same as $A^1$ and $A^2$ in the formula (1), respectively.

From 2 to 6 of $L^1$, $L^2$, $L^3$, $Z^1$, $Z^2$, $A^1$, and $A^2$ may bond to each other to form a polydentate ligand.

The above-mentioned catalyst is generally referred to as "ruthenium-carbene complex", and, for example, ruthenium-carbene complexes described in Vougioukalakis, G. C. et al., Chem. Rev., 2010, 110, 1746-1787 can be used. Also for example, ruthenium-carbene complexes commercially available from Aldrich or Umicore are also usable.

Specific examples of the ruthenium-carbene complex include bis(triphenylphosphine)benzylidene ruthenium dichloride, bis(tricyclohexylphosphine)benzylidene ruthenium dichloride, bis(tricyclohexylphosphine)-3-methyl-2-butenylidene ruthenium dichloride, (1,3-diisopropylimidazol-2-ylidene)(tricyclohexylphosphine)benzylidene ruthenium dichloride, (1,3-dicyclohexylimidazol-2-yldene) (tricyclohexylphosphine)benzylidene ruthenium dichloride, (1,3-dimesitylimidazol-2-ylidene)(tricyclohexylphosphine) benzylidene ruthenium dichloride, (1,3-dimesityl-4,5-dihydroimidazol-2-ylidene)(tricyclohexylphosphine)benzylidene ruthenium dichloride, [1,3-bis(2,6-diisopropylphenyl)-4,5-dihydroimidazol-2-ylidene] (tricyclohexylphosphine)benzylidene ruthenium dichloride, [1,3-bis(2-methylphenyl)-4,5-dihydroimidazol-2-ylidene] (tricyclohexylphosphine)benzylidene ruthenium dichloride, [1,3-dicyclohexyl-4,5-dihydroimidazol-2-ylidene](tricyclohexylphosphine)benzylidene ruthenium dichloride, bis(tricyclohexylphosphine)ethoxymethylidene ruthenium dichloride, (1,3-dimesityl-4,5-dihydroimidazol-2-ylidene) (tricyclohexylphosphine)ethoxymethylidene ruthenium dichloride, (1,3-dimesityl-4,5-dihydroimidazol-2-ylidene) [bis(3-bromopyridine)]benzylidene ruthenium dichloride, (1,3-dimesityl-4,5-dihydroimidazol-2-ylidene)(2-isopropoxyphenylmethylidene) ruthenium dichloride, (1,3-dimesityl-4,5-dihydroimidazol-2-ylidene)[(tricyclohexylphosphoranyl)methylidene] dichlororuthenium tetrafluoroborate, UmicoreM2, UmicoreM51, UmicoreM52, UmicoreM71SIMes, UmicoreM71SIPr, UmicoreM73SIMes, UmicoreM73SIPr, and the like. Especially preferred are (1,3-dimesityl-4,5-dihydroimidazol-2-ylidene)(tricyclohexylphosphine)benzylidene ruthenium dichloride, (1,3-dimesityl-4,5-dihydroimidazol-2-ylidene) (2-isopropoxyphenylmethylidene) ruthenium dichloride, (1,3-dimesityl-4,5-dihydroimidazol-2-ylidene)[(tricyclohexylphosphoranyl)methylidene] dichlororuthenium tetrafluoroborate, UmicoreM51, UmicoreM52, UmicoreM71SIMes, UmicoreM71SIPr, UmicoreM73SIMes, and UmicoreM73SIPr. Of the above-mentioned complexes, the names starting from "Umicore" are trade names of the products by Umicore.

The above-mentioned ruthenium-carbene complexes may be used either singly or used in combination of two or more kinds thereof. Further if desired, these may be used as carried by a carrier such as silica gel, alumina, polymer or the like.

<Compound (2)>

$X^1$ and $X^2$ in the compound (2) each are independently a functional group selected from the group consisting of the functional group (i), the functional group (ii), the functional group (v), and the functional group (vi), and these may bond to each other to form a ring. In the case where one of $X^1$ and $X^2$ is a hydrogen atom, the other is a functional group selected from the group consisting of the functional group (ii), the functional group (v) and the functional group (vi).

That is, $X^1$ and $X^2$ in the compound (2) each are independently a hydrogen atom; a halogen atom; an alkyl group having a carbon number of from 1 to 12; an alkyl group having a carbon number of from 1 to 12 and containing one or more atoms selected from the group consisting of an oxygen atom, a nitrogen atom, a sulfur atom, a phosphorus atom, and a silicon atom; an alkoxy group having a carbon number of from 1 to 12; an alkoxy group having a carbon number of from 1 to 12 and containing one or more atoms selected from the group consisting of an oxygen atom, a nitrogen atom, a sulfur atom, a phosphorus atom, and a silicon atom; an aryl group having a carbon number of from 5 to 20; an aryl group having a carbon number of from 5 to 20 and containing one or more atoms selected from the group consisting of an oxygen atom, a nitrogen atom, a sulfur atom, a phosphorus atom, and a silicon atom; an aryloxy group having a carbon number of from 5 to 20; an aryloxy group having a carbon number of from 5 to 20 and containing one or more atoms selected from the group consisting of an oxygen atom, a nitrogen atom, a sulfur atom, a phosphorus atom, and a silicon atom; a (per)halogenated alkyl group having a carbon number of from 1 to 12; a (per)halogenated alkyl group having a carbon number of from 1 to 12 and containing one or more atoms selected from the group consisting of an oxygen atom, a nitrogen atom, a sulfur atom, a phosphorus atom, and a silicon atom; a (per)halogenated alkoxy group having a carbon number of from 1 to 12; a (per)halogenated alkoxy group having a carbon number of from 1 to 12 and containing one or more atoms selected from the group consisting of an oxygen atom, a nitrogen atom, a sulfur atom, a phosphorus atom, and a silicon atom; a (per)halogenated aryl group having a carbon number of from 5 to 20; a (per)halogenated aryl group having a carbon number of from 5 to 20 and containing one or more atoms selected from the group consisting of an oxygen atom, a nitrogen atom, a sulfur atom, a phosphorus atom, and a silicon atom; a (per)halogenated aryloxy group having a carbon number of from 5 to 20; or a (per)halogenated aryloxy group having a carbon number of from 5 to 20 and containing one or more atoms selected from the group consisting of an oxygen atom, a nitrogen atom, a sulfur atom, a phosphorus atom, and a silicon atom; and these may bond to each other to form a ring. However, the compound excludes a case where both $X^1$ and $X^2$ are hydrogen atoms.

Of the above-mentioned groups, groups having carbon atoms may have an etheric oxygen atom between the carbon atom and the carbon atom as described below.

That is, the compound (2) is an olefin compound having a partial structure of $(CF_2=C)$ in which two fluorine atoms bond to one carbon atom constituting the double bond.

The halogen atom includes a fluorine atom, a chlorine atom, a bromine atom, and an iodine atom. From the viewpoint of availability, preferred are a fluorine atom and a chlorine atom.

The alkyl group having a carbon number of from 1 to 12 is preferably the group having a carbon number of from 1 to 8, and specifically preferred is a methyl group, an ethyl group or a propyl group from the viewpoint of availability. The alkyl group chain may be linear, branched or cyclic.

The alkoxy group having a carbon number of from 1 to 12 is preferably the group having a carbon number of from 1 to 8, and specifically preferred is a methoxy group, an ethoxy group or a propoxy group from the viewpoint of availability. The alkoxy group chain may be linear, branched or cyclic.

The aryl group having a carbon number of from 5 to 20 is preferably the group having a carbon number of from 5 to 12, and specifically preferred is a phenyl group from the viewpoint of availability.

The aryloxy group having a carbon number of from 5 to 20 is preferably the group having a carbon number of from 5 to 12, and especially preferred is an aryloxy group having a carbon number of from 5 to 12. Specifically, a phenyloxy group is preferred from the viewpoint of availability.

The (per)halogenated alkyl group having a carbon number of from 1 to 12 is preferably the group having a carbon number of from 1 to 8, and especially preferred is a (per)fluoroalkyl group having a carbon number of from 1 to 8. Specifically, a trifluoromethyl group, a pentafluoroethyl group or a heptafluoropropyl group is preferred from the viewpoint of availability. The alkyl group chain may be linear, branched or cyclic.

The (per)halogenated alkoxy group having a carbon number of from 1 to 12 is preferably the group having a carbon number of from 1 to 8, and especially preferred is a (per)fluoroalkoxy group having a carbon number of from 1 to 8. Specifically, from the viewpoint of availability, a trifluoromethoxy group, a pentafluoroethoxy group, a heptafluoropropoxy group, a perfluoro(methoxymethoxy) group, or a perfluoro(propoxypropoxy) group is preferred, and a trifluoromethoxy group or a perfluoro(propoxypropoxy) group is especially preferred. The alkoxy group chain may be linear, branched or cyclic.

The (per)halogenated aryl group having a carbon number of from 5 to 20 is preferably the group having a carbon number of from 5 to 12, and especially preferred is a (per)fluoroaryl group having a carbon number of from 5 to 12. Specifically, from the viewpoint of availability, a monofluorophenyl group or a pentafluorophenyl group is preferred, and a pentafluorophenyl group is especially preferred.

The (per)halogenated aryloxy group having a carbon number of from 5 to 20 is preferably the group having a carbon number of from 5 to 12, and especially preferred is a (per)fluoroaryloxy group having a carbon number of from 5 to 12. Specifically, from the viewpoint of availability, a monofluorophenyloxy group or a pentafluorophenyloxy group is preferred, and a pentafluorophenyloxy group is especially preferred.

The alkyl group, the alkoxy group, the aryl group, the aryloxy group, the (per)halogenated alkyl group, the (per)halogenated alkoxy group, the (per)halogenated aryl group, or the (per)halogenated aryloxy group may have a substituent containing one or more atoms selected from the group consisting of an oxygen atom, a nitrogen atom, a sulfur atom, a phosphorus atom, and a silicon atom. Examples of the substituent include a nitrile group, a carboxyl group, and an ester group (an acyloxy group or an alkoxycarbonyl group). In the case where the group has the substituent, the total carbon number in the alkyl group, the alkoxy group, the (per)halogenated alkyl group, and the (per)halogenated alkoxy group is from 1 to 12, and the total carbon number in the aryl group, the aryloxy group, the (per)halogenated aryl group, and the (per)halogenated aryloxy group is from 5 to 20.

The alkyl group, the alkoxy group, the aryl group, the aryloxy group, the (per)halogenated alkyl group, the (per)

halogenated alkoxy group, the (per)halogenated aryl group, or the (per)halogenated aryloxy group may have an etheric oxygen atom between the carbon atom and the carbon atom. That is, as the functional group (vi), preferred is the functional group (v) containing one or more oxygen atoms, and the oxygen atom is more preferably an etheric oxygen atom. In other words, as the functional group (vi), preferred is the following functional group (vii).

Functional group (vii): the functional group (v) having an etheric oxygen atom between the carbon atom and the carbon atom therein.

A preferred combination of $X^1$ and $X^2$ is a combination where $X^1$ is the functional group (i), the functional group (ii), the functional group (v), or the functional group (vii), and $X^2$ is the functional group (ii), the functional group (v) or the functional group (vii).

More preferred is a combination where $X^1$ is a hydrogen atom, a halogen atom, a (per)halogenated alkyl group having a carbon number of from 1 to 12, a (per)halogenated alkyl group having a carbon number of from 1 to 12 and having an etheric oxygen atom between the carbon atom and the carbon atom, a (per)halogenated alkoxy group having a carbon number of from 1 to 12, a (per)halogenated alkoxy group having a carbon number of from 1 to 12 and having an etheric oxygen atom between the carbon atom and the carbon atom, a (per)halogenated aryl group having a carbon number of from 5 to 20, a (per)halogenated aryl group having a carbon number of from 5 to 20 and having an etheric oxygen atom between the carbon atom and the carbon atom, a (per)halogenated aryloxy group having a carbon number of from 5 to 20, or a (per)halogenated aryloxy group having form 5 to 20 carbon atoms and having an etheric oxygen atom between the carbon atom and the carbon atom; and $X^2$ is a halogen atom, an alkyl group having a carbon number of from 1 to 12, an alkyl group having a carbon number of from 1 to 12 and having an etheric oxygen atom between the carbon atom and the carbon atom, an alkoxy group having a carbon number of from 1 to 12, an alkoxy group having a carbon number of from 1 to 12 and having an etheric oxygen atom between the carbon atom and the carbon atom, an aryl group having a carbon number of from 5 to 20, an aryl group having a carbon number of from 5 to 20 and having an etheric oxygen atom between the carbon atom and the carbon atom, a (per)halogenated alkyl group having a carbon number of from 1 to 12, a (per)halogenated alkyl group having a carbon number of from 1 to 12 and having an etheric oxygen atom between the carbon atom and the carbon atom, a (per)halogenated alkoxy group having a carbon number of from 1 to 12, a (per)halogenated alkoxy group having a carbon number of from 1 to 12 and having an etheric oxygen atom between the carbon atom and the carbon atom, a (per)halogenated aryl group having a carbon number of from 5 to 20, a (per)halogenated aryl group having a carbon number of from 5 to 20 and having an etheric oxygen atom between the carbon atom and the carbon atom, a (per)halogenated aryloxy group having a carbon number of from 5 to 20, or a (per)halogenated aryloxy group having form 5 to 20 carbon atoms and having an etheric oxygen atom between the carbon atom and the carbon atom.

Specifically, preferred examples of the compound (2) are the compounds mentioned below.

[Chem. 24]

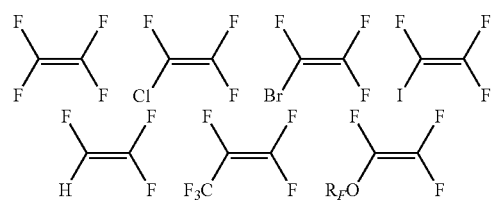

In the above formula, —$OR_F$ represents a (per)halogenated alkoxy group having a carbon number of from 1 to 12, or a (per)halogenated alkoxy group having a carbon number of from 1 to 12 and having an etheric oxygen atom between the carbon atom and the carbon atom.

Specifically, more preferred examples of the compound (2) are the compounds mentioned below.

[Chem. 25]

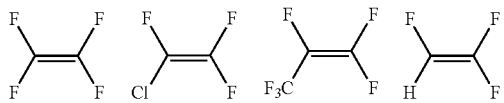

<Compound (7)>

In the compound (7), $A^3$ to $A^6$ each independently represent a functional group selected from the group consisting of the functional group (i), the functional group (ii), the functional group (iii), and the functional group (iv). That is, $A^3$ to $A^6$ each are independently a hydrogen atom, a halogen atom, a monovalent hydrocarbon group having a carbon number of from 1 to 20, or a monovalent hydrocarbon group having a carbon number of from 1 to 20 and containing one or more atoms selected from the group consisting of a halogen atom, an oxygen atom, a nitrogen atom, a sulfur atom, a phosphorus atom, and a silicon atom.

$A^3$ and $A^4$ may bond to each other to form a ring. $A^5$ and $A^6$ may bond to each other to form a ring.

However, the compound (7) excludes a case where both $A^3$ and $A^4$ are halogen atoms and a case where both $A^5$ and $A^6$ are halogen atoms. That is, the compound (7) is an olefin compound but does not include 1,1-dihalogenated olefins.

The halogen atom includes a fluorine atom, a chlorine atom, a bromine atom, and an iodine atom. From the viewpoint of availability, preferred are a fluorine atom and a chlorine atom.

The monovalent hydrocarbon group having a carbon number of from 1 to 20 is preferably an alkyl group having a carbon number of from 1 to 20, an alkoxy group having a carbon number of from 1 to 20, an aryl group having a carbon number of from 5 to 20, or an aryloxy group having a carbon number of from 5 to 20, and from the viewpoint of availability, especially preferred is a methyl group, an ethyl group, a propyl group, a phenyl group, a methoxy group, an ethoxy group, a propoxy group, an isopropoxy group, a butoxy group, a tert-butoxy group, a (2-ethyl)hexyloxy group, or a dodecyloxy group. The hydrocarbon group skeleton may be linear, branched or cyclic.

Preferred examples of the monovalent hydrocarbon group having a carbon number of from 1 to 20 and containing one or more atoms selected from the group consisting of a halogen atom, an oxygen atom, a nitrogen atom, a sulfur atom, a phosphorus atom, and a silicon atom include an alkyl group having a carbon number of from 1 to 20 or alkoxy group having a carbon number of from 1 to 20 which contain the aforementioned atom, and an aryl group having a carbon number of from 5 to 20 or aryloxy group having a carbon number of from 5 to 20 which contain the aforementioned atom. In these preferred groups, a halogen atom may bond to a part of the carbon atoms. That is, for example, the group may be a (per)fluoroalkyl group or a (per)fluoroalkoxy group. Also these preferred groups may have an etheric oxygen atom between the carbon atom and the carbon atom. Also these preferred groups may have a substituent having an oxygen atom, a nitrogen atom, a sulfur atom, a phosphorus atom, or a silicon atom. Examples of the substituent include an amino group, a nitrile group, a carboxyl group, an ester group (an acyloxy group or an alkoxycarbonyl group), a thioalkyl group, and a silyl group.

Above all, from the viewpoint of availability, it is preferred that $A^3$ to $A^6$ each are independently a hydrogen atom, a phenyl group, a methoxy group, an ethoxy group, a propoxy group, an isopropoxy group, a butoxy group, a tert-butoxy group, a (2-ethyl)hexyloxy group, a dodecyloxy group, an acetyl group, a trifluoromethyl group, a pentafluoroethyl group, a heptafluoropropyl group, a perfluorobutyl group, a perfluorohexyl group, or a perfluorooctyl group. It is considered that among the compound (7), a compound having a hetero atom at the vinyl position (compound having any other atom than a carbon atom or a hydrogen atom, at the position adjacent to the carbon atom of olefin) could have an effect of stabilizing the intermediate to be formed during reaction therefore promoting olefin metathesis. Consequently, the compound (7) is preferably a compound having a hetero atom at the vinyl position. The hetero atom preferably existing at the position adjacent to the carbon atom of olefin is preferably an oxygen atom, a nitrogen atom, a sulfur atom, a halogen atom, a phosphorus atom, or a silicon atom, more preferably an oxygen atom, a nitrogen atom or a halogen atom, and even more preferably an oxygen atom or a nitrogen atom.

The compound (7) for use herein may be any of a terminal olefin or an internal olefin. The number of the substituents on the double bond is not specifically limited, but preferred are ethylene, monosubstituted olefins and 1,2-disubstituted olefins as having high reactivity. The geometric isomerism on the double bond is not also specifically limited.

A preferred combination of $A^3$ and $A^4$ is a combination where $A^3$ is a hydrogen atom, and $A^4$ is a hydrogen atom, a monovalent hydrocarbon group having a carbon number of from 1 to 20, or a monovalent hydrocarbon group having a carbon number of from 1 to 20 and containing one or more atoms selected from the group consisting of a halogen atom, an oxygen atom, a nitrogen atom, a sulfur atom, a phosphorus atom, and a silicon atom.

A preferred combination of $A^5$ and $A^6$ is a combination where $A^5$ is a hydrogen atom, and $A^6$ is a hydrogen atom, a hydrogen atom, a monovalent hydrocarbon group having a carbon number of from 1 to 20, or a monovalent hydrocarbon group having a carbon number of from 1 to 20 and containing one or more atoms selected from the group consisting of a halogen atom, an oxygen atom, a nitrogen atom, a sulfur atom, a phosphorus atom, and a silicon atom.

More preferred specific examples of the compound (7) include the compounds mentioned below.

[Chem. 26]

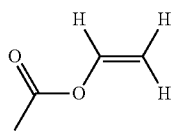

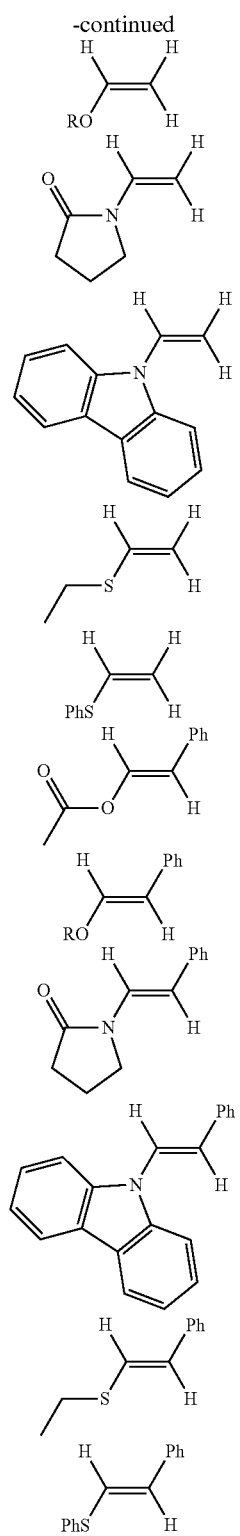

In the above formulae, —OR represents an alkoxy group having a carbon number of from 1 to 12, or an alkoxy group having a carbon number of from 1 to 12 and having an etheric oxygen atom between the carbon atom and the carbon atom.

Especially preferred examples of those compounds (7) include the compounds mentioned below.

[Chem. 27]

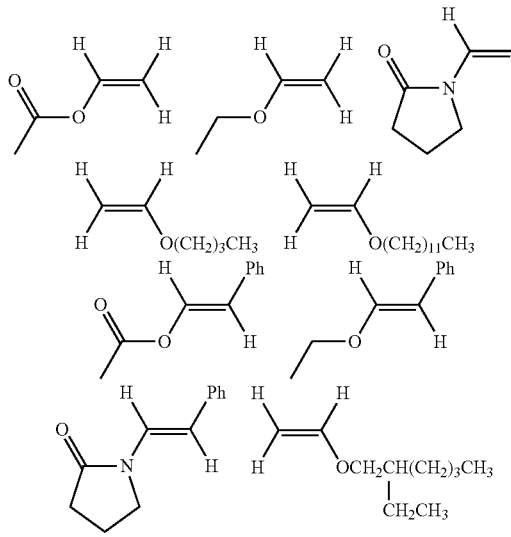

<Compounds (10) to (13)>

Specific examples of the fluorine-containing compound (10) to compound (13) that are obtained through olefin metathesis in the present invention include the compounds mentioned below.

[Chem. 28]

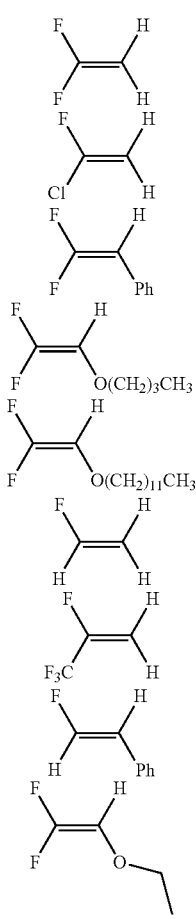

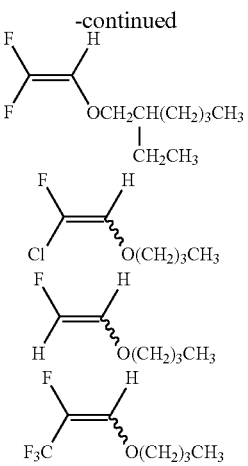

<Production Method>

The present invention relates to a production method for a fluorine-containing olefin through olefin metathesis, in which, typically, two different types of olefins are brought into contact with a ruthenium-carbene complex to conduct olefin metathesis to give an olefin differing from the starting compounds.

Of the olefins as starting materials for use herein, the olefin that is not an olefin in which two fluorine atoms bond to one carbon atom constituting the double bond (the above-mentioned compound (7)) may be any of a terminal olefin or an internal olefin. The number of the substituents on the double bond is not specifically limited, but preferred are ethylene, monosubstituted olefins and 1,2-disubstituted olefins as having high reactivity. The geometric isomerism on the double bond is not also specifically limited. From the viewpoint of increasing the product yield, the olefins degassed and dried are preferably used as starting materials. The degassing operation is not specifically limited. Freeze-pump-thaw degasification or the like may be carried out. The drying operation is not also specifically limited. In general, it may be carried out by bringing into contact with a molecular sieve or the like. The degassing and drying operation for olefins as starting materials are generally conducted before they are brought into contact with the ruthenium-carbene complex.

The olefins as starting materials may contain minor impurities (e.g., peroxides, etc.), and therefore may be purified for the purpose of increasing the product yield. The purification method is not specifically limited. For example, it may be attained according to the methods described in literature (Armarego, W. L. F. et al., Purification of Laboratory Chemicals (Sixth Edition), 2009, Elsevier).

As the olefins where fluorine atoms bond to the carbon atom constituting the double bond (above-mentioned compound (2)) among the fluorine-containing olefins as starting materials, used are terminal olefins. That is, preferred examples thereof include tetrafluoroethylene, hexafluoropropylene, 1,1-difluoro-2-substituted olefins, 1,1,2-trifluoro-2-substituted olefins, 1,1-difluoro-2,2-disubstituted olefins and the like. From the viewpoint of increasing the product yield, the fluorine-containing olefins degassed and dried are preferably used as starting materials. The degassing operation is not specifically limited. Freeze-pump-thaw degasification or the like may be carried out. The drying operation is not also specifically limited. In general, it may be carried out by bringing into contact with a molecular sieve or the like. The degassing and drying operation for fluorine-containing olefins as starting materials are generally conducted before they are brought into contact with the ruthenium-carbene complex.

The fluorine-containing olefins as starting materials may contain minor impurities (e.g., hydrogen fluoride, etc.), and therefore may be purified for the purpose of increasing the product yield. The purification method is not specifically limited. For example, it may be attained according to the methods described in literature (Armarego, W. L. F. et al., Purification of Laboratory Chemicals (Sixth Edition), 2009, Elsevier).

The olefins as starting materials (hereinafter the two types of olefins are collectively referred to as such) may be put into a reactor after they have been previously mixed, or may be put thereinto separately. With a mixture obtained by the contact of the first olefin with the ruthenium-carbene complex may be brought into contact the second olefin.

The molar ratio of the both olefins as starting materials is not specifically limited. In general, based on one mol of one basis olefin, the other olefin is used in an amount of from 0.01 to 100 mol or so, and preferably from 0.1 to 10 mol or so.

The ruthenium-carbene complex (the above-mentioned compound (1), compound (3), compound (4), compound (8), and compound (9)) may be put into as a reagent, or may be generated in the system.

In the case where it is put into as a reagent, a commercially-available ruthenium-carbene complex may be used directly as it is, or a commercially-unavailable ruthenium-carbene complex synthesized from a commercially-available reagent according to a known method may be used.

In the case where it is generated in situ, a ruthenium-carbene complex prepared from a ruthenium complex as a precursor according to a known method may be used in the present invention.

The amount of the ruthenium-carbene complex to be used is not specifically limited. It is used generally from 0.0001 to 1 mol or so, and preferably from 0.001 to 0.2 mol or so, based on one mol of one basis olefin of the olefins as starting materials.

The ruthenium-carbene complex to be used is generally put into the reactor as it is solid, but may be put thereinto after dissolved or suspended in a solvent. The solvent to be used in the case is not specifically limited within a range not having any negative influence on the reaction. An organic solvent, a fluorine-containing organic solvent, an ionic liquid, water and the like may be used either singly or in combination thereof. Of these solvent molecules, a part or all of the hydrogen atoms may be substituted with deuterium atoms.

As the organic solvent, for example, usable are an aromatic hydrocarbon solvent such as benzene, toluene, o-, m- or p-xylene, mesitylene, or the like; an aliphatic hydrocarbon solvent such as hexane, cyclohexane or the like; a halogen-containing solvent such as dichloromethane, chloroform, 1,2-dichloroethane, chlorobenzene, o-dichlorobenzene, or the like; and an ether solvent such as tetrahydrofuran, dioxane, diethyl ether, glyme, diglyme, or the like; and the like. As the fluorine-containing organic solvent, for example, usable are hexafluorobenzene, m-bis(trifluoromethyl)benzene, p-bis(trifluoromethyl)benzene, α,α,α-trifluoromethylbenzene, dichloropentafluoropropane, and the like. As the ionic liquid, for example, usable are various pyridinium salts, various imidazolium salts, and the like. Of the above-mentioned solvents, benzene, toluene, o-, m- or p-xylene, mesitylene, dichloromethane, chloroform, chlorobenzene, o-dichlorobenzene, diethyl ether, dioxane, THF, hexafluorobenzene, m-bis(trifluoromethyl)benzene, p-bis(trifluoromethyl)benzene, α,α,α-trifluoromethylbenzene, or the like, and mixtures thereof are preferred from the viewpoint of the solubility therein of the ruthenium-carbene complex, or the like.

From the viewpoint of increasing the product yield, the solvent degassed and dried is preferably used. The degassing operation is not specifically limited. Freeze-pump-thaw degasification or the like may be carried out. The drying operation is not also specifically limited. In general, it may be brought into contact with a molecular sieve or the like. The degassing and drying operation is generally conducted before it is brought into contact with the ruthenium-carbene complex.

The atmosphere in which olefins and the ruthenium-carbene complex are brought into contact with each other is not specifically limited. From the viewpoint of prolonging the life of the catalyst, preferred is an inert gas atmosphere, and above all, especially preferred is a nitrogen or argon atmosphere. However, for example, in the case where an olefin that is gaseous under reaction conditions, such as ethylene, tetrafluoroethylene or the like, are used as the starting material, the gaseous atmosphere of these can be employed.

The phase for contact between olefins and the ruthenium-carbene complex is not specifically limited. From the viewpoint of the reaction speed, generally employed is a liquid phase. In the case where the olefins as starting materials are gaseous under the reaction condition, the reaction is difficult to carry out in a liquid phase, and therefore may be carried out in a gaseous-liquid two-phase system. For the reaction in a liquid phase, a solvent may be used. As the solvent for use in the case, use can be made of the same as the solvent used for dissolving or suspending the ruthenium-carbene complex. In the case where at least one of the olefins as starting materials is liquid under the reaction condition, the reaction may be carried out in the absence of a solvent.

The container in which olefins and the ruthenium-carbene complex are brought into contact with each other is not specifically limited within a range not having any negative influence on the reaction. For example, metal containers, glass containers and the like are usable. In olefin metathesis according to the present invention, olefins that are gaseous under the reaction condition may be processed, and therefore preferred are airtightly-closable pressure-proof containers.

The temperature at which olefins and the ruthenium-carbene complex are brought into contact with each other is not specifically limited. In general, it may be carried out in a range of from −100 to 200° C., and from the viewpoint of the reaction speed, it is preferably from 0 to 150° C. As the case may be, the reaction could not start at low temperatures, and the complex would rapidly decompose at high temperatures, and consequently, the lower limit and the upper limit of the temperature range must be defined case by case. In general, the reaction may be carried out at a temperature not higher than the boiling point of the solvent used.

The time for which olefins and the ruthenium-carbene complex are brought into contact with each other is not specifically limited. In general, the reaction is carried out in a range of from 1 minute to 48 hours.

The pressure under which olefins and the ruthenium-carbene complex are brought into contact with each other is not specifically limited. The reaction may be carried out under elevated pressure, under normal pressure or under reduced pressure. In general, it is from 0.001 to 10 MPa or so, and preferably from 0.01 to 1 MPa or so.

In the contact of olefins with the ruthenium-carbene complex, an inorganic salt, an organic compound, a metal complex or the like may be made to exist in the system within a range not having any negative influence on the reaction. Also within a range not having any negative influence on the reaction, the mixture of olefins and the ruthenium-carbene complex may be stirred. In stirring method in this case, usable is a mechanical stirrer, a magnetic stirrer or the like.

After olefins and the ruthenium-carbene complex have been brought into contact with each other, the intended object may be obtained generally as a mixture of plural olefins Therefore, it may be isolated according to a known method. Examples of the isolation method include distillation, column chromatography, recycling preparative HPLC, and the like. If desired, these may be employed either singly or in combination of plural kinds thereof.

The intended object obtained in this reaction may be identified according to known methods that are the same as the methods for ordinary organic compounds. For example, there are mentioned $^1$H-, $^{19}$F- or $^{13}$C-NMR, GC-MS, and the like. If desired, these may be employed either singly or in combination of plural kinds thereof.

EXAMPLES

The present invention is described concretely hereinunder with reference to Examples given below, but the present invention is not limited to these.

<Commercial Reagents>

In the Examples, as for the catalyst, commercial products were used in the reaction directly as they are, unless otherwise specifically indicated. Also as for the solvents (benzene, benzene-$d_6$ and m-xylene-$d_{10}$) and the internal standard (m-bis(trifluoromethyl)benzene, p-bis(trifluoromethyl)benzene and α,α,α-trifluoromethylbenzene), commercial products were previously degassed by freeze-pump-thaw cycles, then dried with Molecular Sieve 4A, and used in the reaction, unless otherwise specifically indicated.

<Evaluation Method>

The structure of the compound synthesized in the Examples was identified through measurement of $^1$H-NMR, $^{19}$F-NMR or $^{13}$C-NMR using a nuclear magnetic resonance apparatus (JNM-AL300) manufactured by JEOL. The molecular weight was measured according to an electron ionization method (EI) or a chemical ionization method (CI) using a gas chromatography mass spectrometer (GCMS-QP5000V2 or GCMS-QP2010Ultra) manufactured by Shimadzu.

Example 1

Metathesis of (1,3-dimesityl-4,5-dihydroimidazol-2-ylidene)(tricyclohexylphosphine)benzylidene ruthenium dichloride with tetrafluoroethylene In a nitrogen atmosphere, (1,3-dimesityl-4,5-dihydroimidazol-2-ylidene)(tricyclohexylphosphine)benzylidene ruthenium dichloride (31.8 mg, 0.0375 mmol) and benzene-$d_6$ (1.5 mL) were weighed and put into a 30-mL pressure-proof reactor. Cooled at −78° C., the content solution was frozen, and the internal pressure was reduced to about 1 mmHg. Subsequently, at room temperature, a mixed gas of tetrafluoroethylene/nitrogen (60/40 vol %) was introduced up to 1.7 atm (1.0 atom as a tetrafluoroethylene partial pressure).

The reactor was heated at 60° C., and the reaction was conducted at the temperature for 1 hour. After the completion of the reaction, NMR of the content liquid was measured to confirm the formation of β,β-difluorostyrene and (1,3-dimesityl-4,5-dihydroimidazol-2-ylidene)(tricyclohexylphosphine)difluoromethylidene ruthenium dichloride.

The series of reaction is shown below.

[Chem. 29]

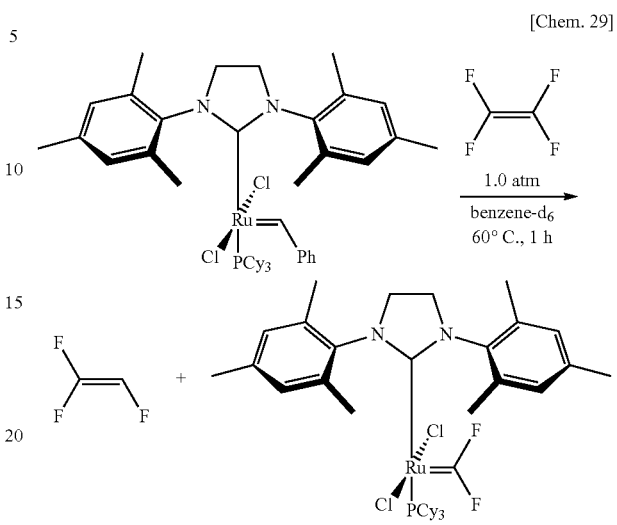

To identify the compounds obtained through the series of reaction, β,β-difluorostyrene was synthesized with reference to a known method. In addition, also with reference to a known method (Non-Patent Document 3, reaction scheme shown below), (1,3-dimesityl-4,5-dihydroimidazol-2-ylidene)(tricyclohexylphosphine)difluoromethylidene ruthenium dichloride was synthesized. The evaluation results are shown below. These were taken as authentic spectra, and since the NMR spectra of the content liquid (mixture) obtained in the above were consistent therewith, it was confirmed the formation of β,β-difluorostyrene and (1,3-dimesityl-4,5-dihydroimidazol-2-ylidene)(tricyclohexylphosphine)difluoromethylidene ruthenium dichloride.

[Chem. 30]

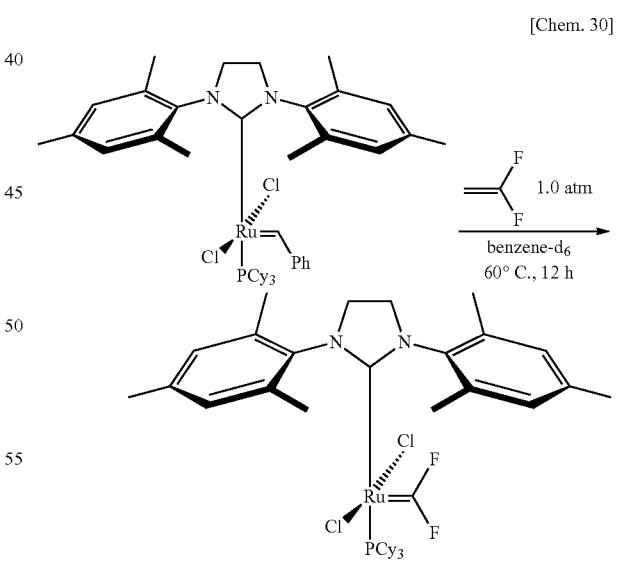

β,β-difluorostyrene $^1$H-NMR (benzene-$d_6$, 300 MHz, tetramethylsilane): δ (ppm) 4.81 (1H, dd, J=26 Hz, 4 Hz), 6.98-7.06 (5H, m).

$^{19}$F-NMR (benzene-$d_6$, 283 MHz, trichlorofluoromethane): δ (ppm) −83.3 (1F, dd, J=32 Hz, 26 Hz), −84.9 (1F, dd, J=32 Hz, 4 Hz).

GC-MS(EI): M$^+$=140.

(1,3-dimesityl-4,5-dihydroimidazol-2-ylidene)(tricyclohexylphosphine)difluoromethylidene ruthenium dichloride $^1$H-NMR (benzene-$d_6$, 300 MHz, tetramethylsilane): δ (ppm) 1.00-1.36 (15H, br m), 1.45-1.69 (9H, br m), 1.82-1.98 (6H, br m), 2.12 (3H, s), 2.12 (3H, s), 2.13 (3H, s), 2.63-2.67 (3H, br m), 2.65 (6H, s), 2.73 (6H, s), 3.29 (4H, s), 6.82 (2H, s), 6.83 (2H, s).

$^{19}$F-NMR (benzene-$d_6$, 283 MHz, trichlorofluoromethane): δ (ppm) −217.0 (2F).

$^{13}$C-NMR (benzene-$d_6$, 75 MHz, residual solvent peak) δ (ppm) 19.1, 20.3, 21.2, 26.6, 28.1, 28.2, 29.8, 30.0, 32.9, 33.1, 51.5, 52.3, 127.7, 128.1, 128.4, 129.8, 130.2, 134.3, 136.5, 138.6, 138.7, 139.3, 216.8 (d, J=85 Hz), 217.8 (td, J=428 Hz, 14 Hz).

Example 2

Metathesis of (1,3-dimesityl-4,5-dihydroimidazol-2-ylidene)(tricyclohexylphosphine)benzylidene ruthenium dichloride and chlorotrifluoroethylene In a nitrogen atmosphere, (1,3-dimesityl-4,5-dihydroimidazol-2-ylidene)(tricyclohexylphosphine)benzylidene ruthenium dichloride (31.8 mg, 0.0375 mmol) and benzene-$d_6$ (1.5 mL) were weighed and put into a 30-mL pressure-proof reactor. Cooled at −78° C., the content liquid was frozen, and the internal pressure was reduced to about 1 mmHg. Subsequently, at room temperature, chlorotrifluoroethylene was introduced up to 1.0 atm.

The reactor was heated at 60° C., and the reaction was conducted at the temperature for 1 hour. After the completion of the reaction, NMR and GC-MS of the content liquid were measured to confirm the formation of β,β-difluorostyrene and β-chloro-β-fluorostyrene (E/Z mixture).

The series of reaction is shown below.

[Chem. 31]

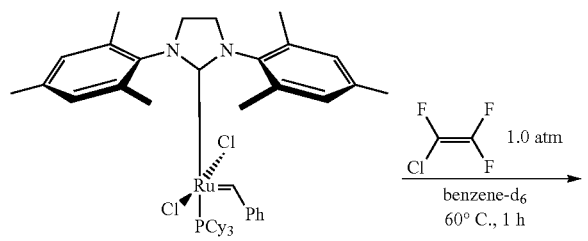

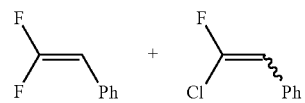

(E)-β-chloro-β-fluorostyrene $^1$H-NMR (CDCl$_3$, 300 MHz, tetramethylsilane): δ (ppm) 5.42 (1H, d, J=30 Hz), 7.20-7.45 (5H, m).

$^{19}$F-NMR (CDCl$_3$, 283 MHz, trichlorofluoromethane): δ (ppm) −74.4 (1F, d, J=30 Hz).

GC-MS(EI): M$^+$=156.

(Z)-β-chloro-β-fluorostyrene $^1$H-NMR (CDCl$_3$, 300 MHz, tetramethylsilane): δ (ppm) 6.00 (1H, d, J=13 Hz), 7.20-7.45 (5H, m).

$^{19}$F-NMR (CDCl$_3$, 283 MHz, trichlorofluoromethane): δ (ppm) −71.5 (1F, d, Hz).

GC-MS(EI): M$^+$=156

Example 3

Metathesis of (1,3-dimesityl-4,5-dihydroimidazol-2-ylidene)(tricyclohexylphosphine)benzylidene ruthenium dichloride and hexafluoropropylene In a nitrogen atmosphere, (1,3-dimesityl-4,5-dihydroimidazol-2-ylidene)(tricyclohexylphosphine)benzylidene ruthenium dichloride (5.1 mg, 0.006 mmol) and m-xylylene-$d_{10}$ (0.16 mL) with p-bis(trifluoromethyl)benzene (internal standard, 0.06 mmol) dissolved therein were weighed and put into a pressure-proof NMR tube. The content liquid was frozen by cooling with liquid nitrogen, and the internal pressure was reduced to about 1 mmHg. Subsequently, at room temperature, hexafluoropropylene (1.0 atm, 1.35 mL, 0.06 mmol) was introduced thereinto.

The NMR tube was heated at 60° C., and the reaction was conducted at the temperature for 1 hour. Subsequently, this was further heated at 100° C. for 1 hour and 140° C. for 1 hour in that order. The reaction proceeding was traced through NMR measurement to confirm the formation of β-fluoro-β-trifluoromethylstyrene (E/Z mixture).

The series of reaction is shown below.

[Chem. 32]

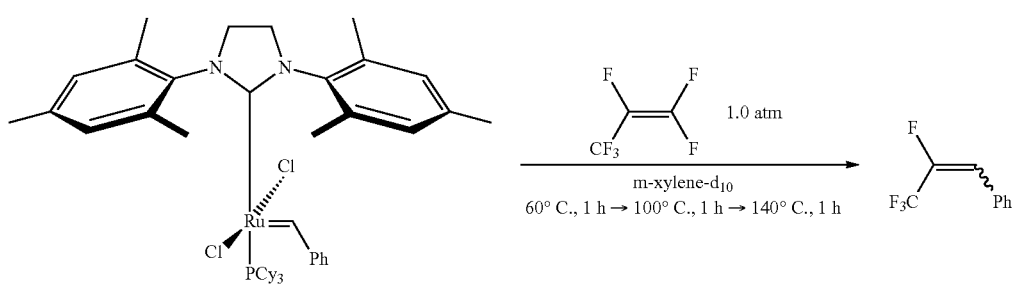

β-fluoro-β-trifluoromethylstyrene (E/Z mixture)
GC-MS(CI): [M+H]+=191

Example 4

Metathesis of (1,3-dimesityl-4,5-dihydroimidazol-2-ylidene)(tricyclohexylphosphine)benzylidene ruthenium dichloride and compound A In a nitrogen atmosphere, a compound A ($CF_2$=CF—O—$CF_2$CF($CF_3$)—O—$CF_2CF_2CF_3$: 864 mg, 2 mmol), (1,3-dimesityl-4,5-dihydroimidazol-2-ylidene)(tricyclohexylphosphine)benzylidene ruthenium dichloride (10 mol %, 0.2 mmol, 169.8 mg) and toluene (dried commercial product, 4 mL) were put into a 20-mL recovery flask equipped with a magnetic stirrer bar. The mixture was degassed by freeze-pump-thaw cycles, and then heated at 100° C. for 2 hours.

After the completion of the heating, the reaction solution was analyzed through NMR measurement, which confirmed the formation of β,β-difluorostyrene and (1,3-dimesityl-4,5-dihydroimidazol-2-ylidene)(tricyclohexylphosphine)difluoromethylidene ruthenium dichloride. From the crude product obtained through evaporation of the solvent under reduced pressure, a compound B and a compound C (PhCH=CF—O—$CF_2$CF($CF_3$)—O—$CF_2CF_2CF_3$) were isolated by using silica gel column chromatography and recycling preparative HPLC. The compound B and the compound C are geometric isomers (E/Z), and the isolated yield as combined was 11% based on the compound A.

The series of the reactions is shown below, along with the structures of the compound A to the compound C.

[Chem. 33]

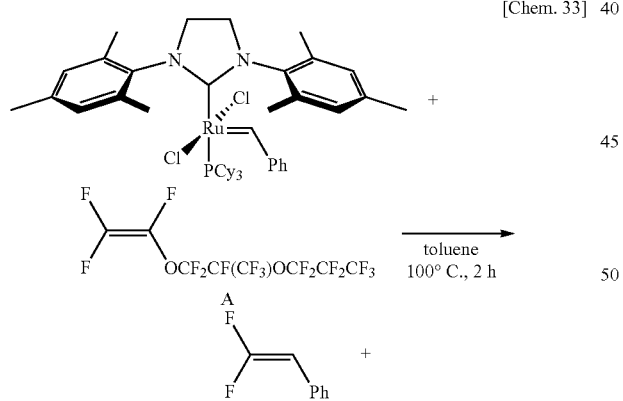

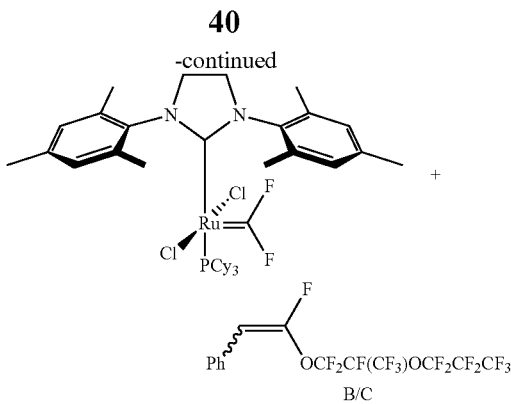

The evaluation results of the resultant compound B and compound C are shown below.

(Compound B)
$^1$H-NMR (CDCl$_3$, 300 MHz, tetramethylsilane): δ (ppm) 5.59 (1H, d, J=27 Hz), 7.27-7.46 (5H, m).
$^{19}$F-NMR (CDCl$_3$, 283 MHz, trichlorofluoromethane): δ (ppm) −80.4 (3F), −81.7 (3F), −82.0 (1F), −82.2 (1F), −82.7 (1F), −84.8 (2F), −130.0 (2F), −145.4 (1F).
GC-MS(EI): M$^+$=472.

(Compound C)
$^1$H NMR(CDCl$_3$, 300 MHz, tetramethylsilane): δ (ppm) 5.87 (1H, d, J=7 Hz), 7.26-7.40 (5H, m).
$^{19}$F-NMR (CDCl$_3$, 283 MHz, trichlorofluoromethane): δ (ppm) −80.1 (3F), −81.7 (4F), −82.1 (1F), −83.1 (1F), −83.3 (1F), −84.9 (1F), −129.9 (2F), −145.0 (1F).
GC-MS(EI): M$^+$=472.

Example 5

Metathesis of (1,3-dimesityl-4,5-dihydroimidazol-2-ylidene)(tricyclohexylphosphine)difluoromethylidene ruthenium dichloride with vinyl acetate In a nitrogen atmosphere, vinyl acetate (8.6 mg, 0.1 mmol), (1,3-dimesityl-4,5-dihydroimidazol-2-ylidene)(tricyclohexylphosphine)difluoromethylidene ruthenium dichloride (10 mol %, 0.01 mmol, 8.1 mg) synthesized with reference to a known method (Non-Patent Document 3), and m-xylene-d$_{10}$ (0.6 mL) were put in an NMR tube. These were mixed uniformly, and heated at 60° C. for 1 hour. Subsequently, this was further heated at 100° C. for 1 hour and 140° C. for 1 hour in that order. The reaction proceeding was traced through NMR measurement to confirm the formation of vinylidene fluoride after the heating at 140° C. for 1 hour.

The series of reaction is shown below.

[Chem. 34]

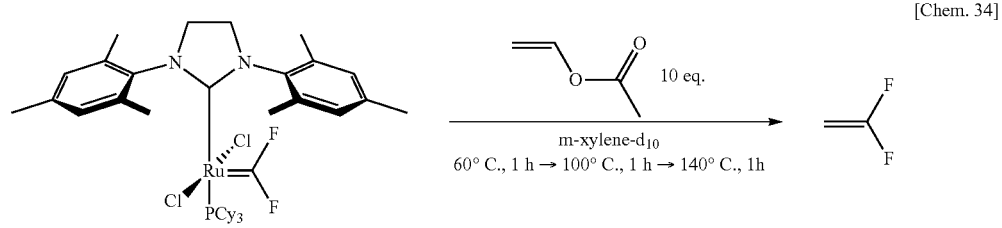

41

The evaluation results of a commercially available vinylidene fluoride are shown below. These were taken as authentic spectra, and since the NMR spectra of the content liquid (mixture) obtained in the above were consistent therewith, it was confirmed the formation of vinylidene fluoride.

$^1$H-NMR (m-xylene-$d_{10}$, 300 MHz, tetramethylsilane): δ (ppm) 3.21-3.52 (2H,
$^{19}$F-NMR (m-xylene-$d_{10}$, 283 MHz, trichlorofluoromethane): δ (ppm) −81.6--81.9 (2F, m).

Example 6

Metathesis of (1,3-dimesityl-4,5-dihydroimidazol-2-ylidene)(tricyclohexylphosphine)difluoromethylidene ruthenium dichloride with ethyl vinyl ether In a nitrogen atmosphere, ethyl vinyl ether (7.2 mg, 0.1 mmol), (1,3-dimesityl-4,5-dihydroimidazol-2-ylidene)(tricyclohexylphosphine)difluoromethylidene ruthenium dichloride (10 mol %, 0.01 mmol, 8.1 mg) synthesized with reference to a known method (Non-Patent Document 3), and m-xylene-$d_{10}$ (0.6 mL) were put in an NMR tube. These were mixed uniformly, and heated at 60° C. for 1 hour. Subsequently, this was further heated at 100° C. for 1 hour and 140° C. for 1 hour in that order. The reaction proceeding was traced through NMR measurement to confirm the formation of vinylidene fluoride after the heating at 60° C. for 1 hour.

The series of reaction is shown below.

[Chem. 35]

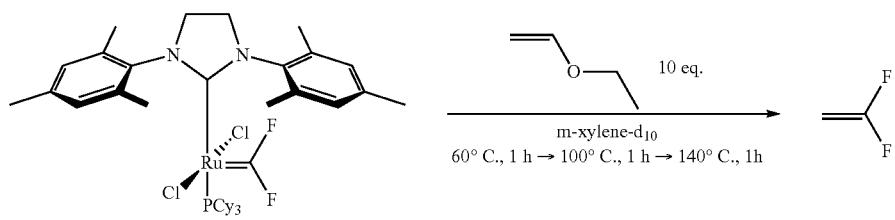

Example 7

Metathesis of (1,3-dimesityl-4,5-dihydroimidazol-2-ylidene)(tricyclohexylphosphine)difluoromethylidene ruthenium dichloride with β-ethoxystyrene In a nitrogen atmosphere, β-ethoxystyrene (E/Z mixture, 14.8 mg, 0.1 mmol—this was previously degassed by freeze-pump-thaw cycles and dried with Molecular Sieve 4A) synthesized with reference to a known method, (1,3-dimesityl-4,5-dihydroimidazol-2-ylidene)(tricyclohexylphosphine)difluoromethylidene ruthenium dichloride (10 mol %, 0.01 mmol, 8.1 mg) synthesized with reference to a known method (Non-Patent Document 3), and m-xylene-$d_{10}$ (0.6 mL) were put in an NMR tube. These were mixed uniformly, and heated at 60° C. for 1 hour. Subsequently, this was further heated at 100° C. for 1 hour and 140° C. for 1 hour in that order. The reaction proceeding was traced through NMR measurement to confirm the formation of β,β-difluorostyrene.

The series of reaction is shown below.

[Chem. 36]

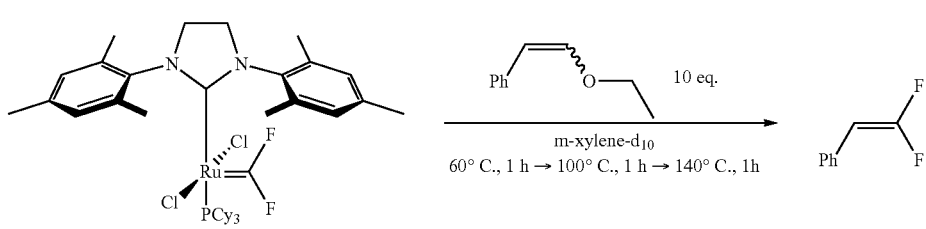

Example 8

Metathesis of (2-ethylhexyl) vinyl ether with tetrafluoroethylene by (1,3-dimesityl-4,5-dihydroimidazol-2-ylidene)(tricyclohexylphosphine)difluoromethylidene ruthenium dichloride In a nitrogen atmosphere, (1,3-dimesityl-4,5-dihydroimidazol-2-ylidene)(tricyclohexylphosphine)difluoromethylidene ruthenium dichloride (10 mol %, 0.006 mmol) synthesized with reference to a known method (Non-Patent Document 3), (2-ethylhexyl) vinyl ether (0.06 mmol, —this was previously degassed by freeze-pump-thaw cycles and dried with Molecular Sieve 4A), and benzene-$d_6$ (0.17 mL) with m-bis(trifluoromethyl)benzene (internal standard, 0.06 mmol) dissolved therein were weighed and put in a pressure-proof NMR tube. The content liquid was frozen by cooling with liquid nitrogen, and the internal pressure was reduced to about 1 mmHg. Subsequently, at room temperature, tetrafluoroethylene (1.0 atm, 1.35 mL, 0.06 mmol) was introduced thereinto.

The NMR tube was heated at 60° C., and the reaction was conducted at the temperature for 24 hours. The reaction proceeding was traced through NMR measurement to confirm the formation of vinylidene fluoride and (2,2-difluorovinyl) (2'-ethylhexyl) ether.

The series of reaction is shown below. The catalyst turnover number, as calculated from the $^{19}$F-NMR spectrum (internal standard: m-bis(trifluoromethyl)benzene), was 6.5.

[Chem. 37]

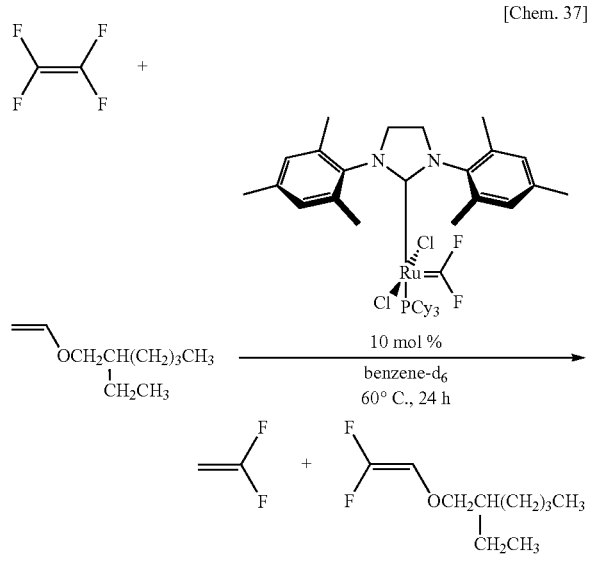

Example 9

Metathesis of Butyl Vinyl Ether with Tetrafluoroethylene by Commercially Available Ruthenium Catalyst In a nitrogen atmosphere, a commercially available ruthenium catalyst (2 mol %, 0.0012 mmol), butyl vinyl ether (0.06 mmol—this was previously degassed by freeze-pump-thaw cycles and dried with Molecular Sieve 4A), and benzene-$d_6$ (0.6 mL) with p-bis(trifluoromethyl)benzene (internal standard, 0.02 mmol) dissolved therein were weighed and put in a pressure-proof NMR tube. Subsequently, the vapor phase part in the NMR tube was substituted with tetrafluoroethylene (1.0 atm, 2.7 mL, 0.12 mmol).

The NMR tube was heated at 60° C., and the reaction was conducted at the temperature for 1 hour. After the completion of the reaction, NMR and GC-MS of the content liquid were measured to confirm the formation of vinylidene fluoride and butyl (2,2-difluorovinyl) ether.

The series of reaction is shown below.

The structures 9A to 9J of the commercially available ruthenium catalysts and the catalyst turnover number (catalyst turnover frequency per hour), as calculated from the $^{19}$F-NMR spectrum (internal standard: p-bis(trifluoromethyl)benzene), are shown in Table 1.

[Chem. 38]

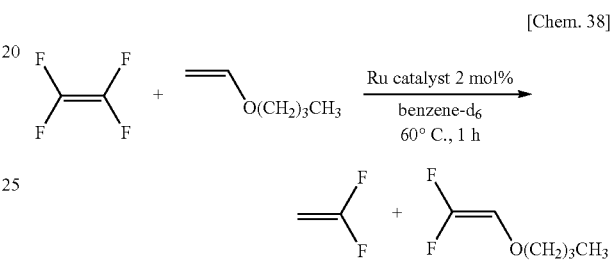

TABLE 1

| Ex. | Structure | Catalyst Turnover Freq. |
|---|---|---|
| 9A | 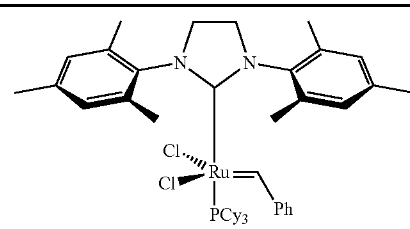 | 0.7 |
| 9B | 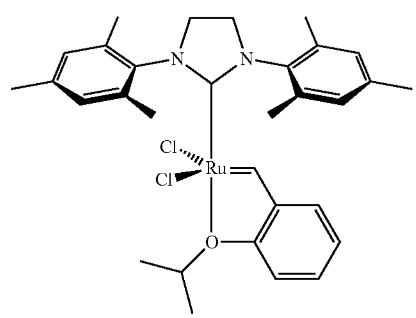 | 3.4 |
| 9C | 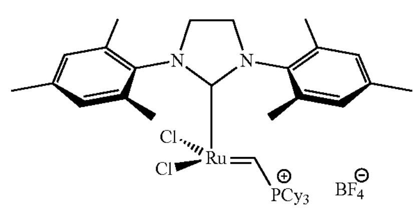 | 4.4 |

TABLE 1-continued

| Ex. | Structure | Catalyst Turnover Freq. |
|---|---|---|
| 9D | Umicore M51 | 3.9 |
| 9E | Umicore M52 | 4.6 |
| 9F | Umicore M71 SIMes | 3.4 |
| 9G | Umicore M71 SIPr | 4.0 |
| 9H | Umicore M73 SIMes | 5.0 |
| 9J | Umicore M73 SIPr | 6.0 |

Example 10

Metathesis of Butyl Vinyl Ether with Tetrafluoroethylene by UmicoreM73SIPr Catalyst In a nitrogen atmosphere, UmicoreM73SIPr catalyst (10 mol %, 0.006 mmol), butyl vinyl ether (0.06 mmol—this was previously degassed by freeze-pump-thaw cycles and dried with Molecular Sieve 4A), and benzene-$d_6$ (0.6 mL) with p-bis(trifluoromethyl)benzene (internal standard, 0.02 mmol) dissolved therein were weighed and put in an NMR tube. Subsequently, the vapor phase part in the NMR tube was substituted with tetrafluoroethylene (1.0 atm, 2.7 mL, 0.12 mmol).

The NMR tube was heated at 60° C., and the reaction was conducted at the temperature for 1 hour. After the completion of the reaction, NMR and GC-MS of the content liquid were measured to confirm the formation of butyl (2,2-difluorovinyl) ether and vinylidene fluoride.

The series of reaction is shown below. The catalyst turnover number (catalyst turnover frequency per hour), as calculated from the $^{19}$F-NMR spectrum (internal standard: p-bis(trifluoromethyl)benzene), was 2.5.

[Chem. 39]

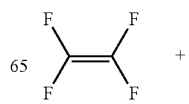 +

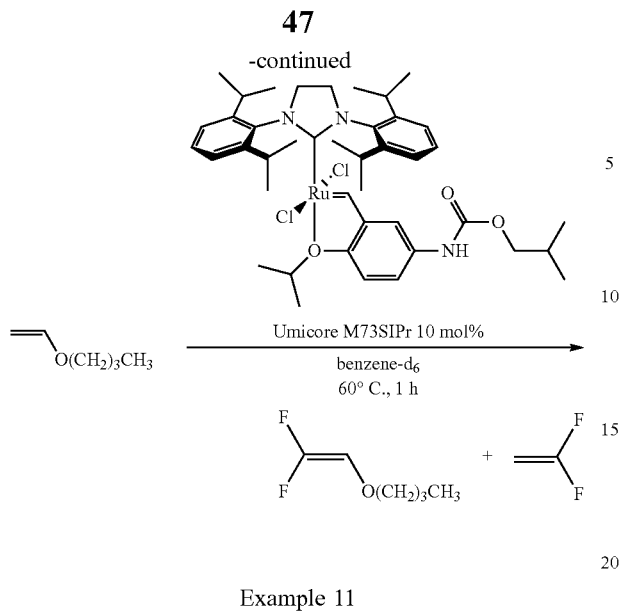

Example 11

Metathesis of Butyl Vinyl Ether with Chlorotrifluoroethylene by UmicoreM73SIPr Catalyst In a nitrogen atmosphere, UmicoreM73SIPr catalyst (10 mol %, 0.006 mmol), butyl vinyl ether (0.06 mmol—this was previously degassed by freeze-pump-thaw cycles and dried with Molecular Sieve 4A), and benzene-$d_6$ (0.6 mL) with p-bis(trifluoromethyl)benzene (internal standard, 0.02 mmol) dissolved therein were weighed and put in an NMR tube. Subsequently, the vapor phase part in the NMR tube was substituted with chlorotrifluoroethylene (1.0 atm, 2.7 mL, 0.12 mmol).

The NMR tube was heated at 60° C., and the reaction was conducted at the temperature for 1 hour. After the completion of the reaction, NMR and GC-MS were measured to confirm the formation of butyl (2,2-difluorovinyl) ether, butyl (2-chloro-2-fluorovinyl) ether (E/Z mixture), 1-chloro-1-fluoroethylene, and vinylidene fluoride.

The series of reaction is shown below. The catalyst turnover number (catalyst turnover frequency per hour), as calculated from the $^{19}$F-NMR spectrum (internal standard: p-bis(trifluoromethyl)benzene), was 2.2.

[Chem. 40]

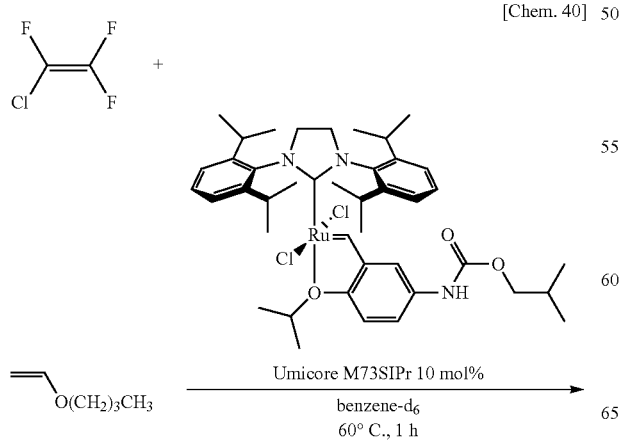

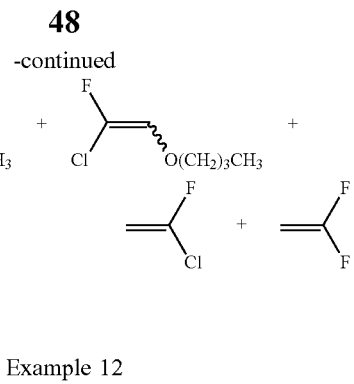

Example 12

Metathesis of Butyl Vinyl Ether with Hexafluoropropylene by UmicoreM73SIPr Catalyst In a nitrogen atmosphere, UmicoreM73SIPr catalyst (10 mol %, 0.006 mmol), butyl vinyl ether (0.06 mmol—this was previously degassed by freeze-pump-thaw cycles and dried with Molecular Sieve 4A), and benzene-$d_6$ (0.6 mL) with p-bis(trifluoromethyl)benzene (internal standard, 0.02 mmol) dissolved therein were weighed and put in an NMR tube. Subsequently, the vapor phase part in the NMR tube was substituted with hexafluoropropylene (1.0 atm, 2.7 mL, 0.12 mmol).

The NMR tube was heated at 60° C., and the reaction was conducted at the temperature for 1 hour. After the completion of the reaction, NMR and GC-MS of the content liquid were measured to confirm the formation of butyl (2,3,3,3-tetrafluoropropen-1-yl) ether (E/Z mixture) and vinylidene fluoride. In this case, formation of neither butyl (2,2-difluorovinyl) ether nor 2,3,3,3-tetrafluoro-1-propene was observed.

The series of reaction is shown below. The catalyst turnover number (catalyst turnover frequency per hour), as calculated from the $^{19}$F-NMR spectrum (internal standard: p-bis(trifluoromethyl)benzene), was 0.6.

[Chem. 41]

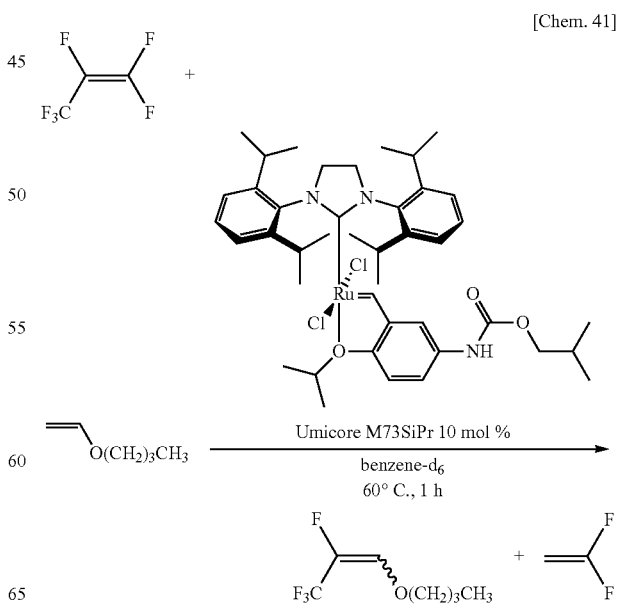

Example 13

Metathesis of Butyl Vinyl Ether with Trifluoroethylene by UmicoreM73 SIPr Catalyst In a nitrogen atmosphere, UmicoreM73SIPr catalyst (10 mol %, 0.006 mmol), butyl vinyl ether (0.06 mmol—this was previously degassed by freeze-pump-thaw cycles and dried with Molecular Sieve 4A), and benzene-$d_6$ (0.6 mL) with p-bis(trifluoromethyl)benzene (internal standard, 0.02 mmol) dissolved therein were weighed and put in an NMR tube. Subsequently, the vapor phase part in the NMR tube was substituted with a mixed gas of trifluoroethylene/nitrogen (80/20 vol %, 1.0 atm, 2.7 mL, 0.096 mmol as trifluoroethylene).

The NMR tube was heated at 60° C., and the reaction was conducted at the temperature for 1 hour. After the completion of the reaction, NMR and GC-MS of the content liquid were measured to confirm the formation of butyl (2-fluorovinyl) ether (E/Z mixture) and vinylidene fluoride. In this case, formation of neither butyl (2,2-difluorovinyl) ether nor vinylidene fluoride was observed.

The series of reaction is shown below. The catalyst turnover number (catalyst turnover frequency per hour), as calculated from the $^{19}$F-NMR spectrum (internal standard: p-bis(trifluoromethyl)benzene), was 3.2.

[Chem. 42]

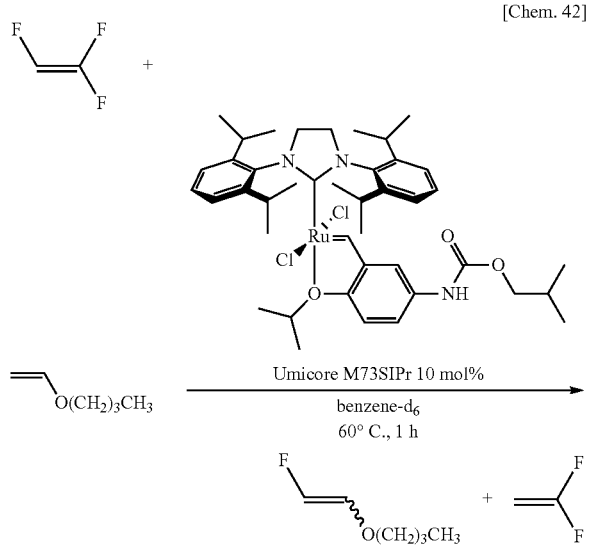

Example 14

Metathesis of Dodecyl Vinyl Ether with Tetrafluoroethylene by UmicoreM73SIPr Catalyst In a nitrogen atmosphere, UmicoreM73SIPr catalyst (10 mol %, 0.10 mmol, 82.6 mg), benzene (5.0 mL), dodecyl vinyl ether (1.0 mmol, 212.4 mg) previously dried with potassium hydroxide, and α,α,α-trifluoromethylbenzene (internal standard, 0.33 mmol, 48.7 mg) were weighed and put in a 30-mL pressure-proof reactor. The content liquid was frozen by cooling with liquid nitrogen, and the internal pressure was reduced to about 1 mmHg. Subsequently, at room temperature, tetrafluoroethylene (8.2 atm, 10 mmol) was introduced thereinto.

The reactor was heated at 60° C. and the reaction was conducted at the temperature for 1 hour. After the completion of the reaction, (2,2-difluorovinyl) dodecyl ether was isolated from the resultant crude product through silica gel column chromatography and recycling preparative HPLC (0.145 g, 0.58 mmol, 58%). In this case, the catalyst turnover number was 5.8.

The series of reaction is shown below.

[Chem. 43]

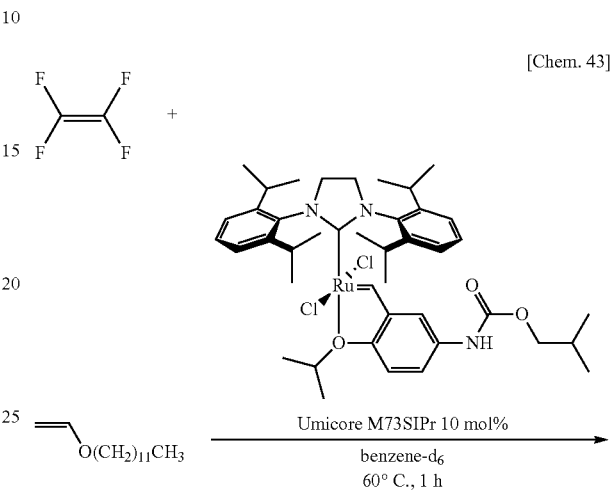

The evaluation results of the resultant (2,2-difluorovinyl) dodecyl ether are shown below.

$^1$H-NMR (benzene-$d_6$, 300 MHz, tetramethylsilane): δ (ppm) 0.92 (3H, t, J=7 Hz), 1.14-1.41 (20H, br m), 3.22 (2H, t, J=7 Hz), 5.19 (1H, dd, J=16 Hz, 3 Hz).

$^{19}$F-NMR (benzene-$d_6$, 283 MHz, trichlorofluoromethane): δ (ppm) -102.1 (1F, dd, J=82 Hz, 16 Hz), -122.6 (1F, dd, J=82 Hz, 3 Hz).

$^{13}$C-NMR (benzene-$d_6$, 75 MHz, residual solvent peak): δ (ppm) 14.3 (s), 23.2 (s), 26.0 (s), 29.6 (s), 29.7 (s), 29.9 (s), 30.0 (s), 30.1 (s), 30.1 (s), 30.1 (s), 32.4 (s), 73.5 (dd, J=2 Hz, 2 Hz), 108.5 (dd, J=53 Hz, 15 Hz), 155.8 (dd, J=288 Hz, 274 Hz).

GC-MS(EI): M$^+$=248.

Example 15

Metathesis of β-Ethoxystyrene with Tetrafluoroethylene by UmicoreM73SIPr Catalyst In a nitrogen atmosphere, UmicoreM73SIPr catalyst (10 mol %, 0.006 mmol), β-ethoxystyrene (E/Z mixture, 0.06 mmol—this was previously degassed by freeze-pump-thaw cycles and dried with Molecular Sieve 4A) synthesized with reference to a known method, and m-xylylene-$d_{10}$ (0.6 mL) with p-bis(trifluoromethyl)benzene (internal standard, 0.02 mmol) dissolved therein were weighed and put in an NMR tube. Subsequently, the vapor phase part in the NMR tube was substituted with tetrafluoroethylene (1.0 atm, 2.7 mL, 0.12 mmol).

The NMR tube was heated at 140° C., and the reaction was conducted at the temperature for 1 hour. After the completion of the reaction, NMR and GC-MS of the content liquid were measured to confirm the formation of β,β-difluorostyrene and (2,2-difluorovinyl) ethyl ether.

The series of reaction is shown below.

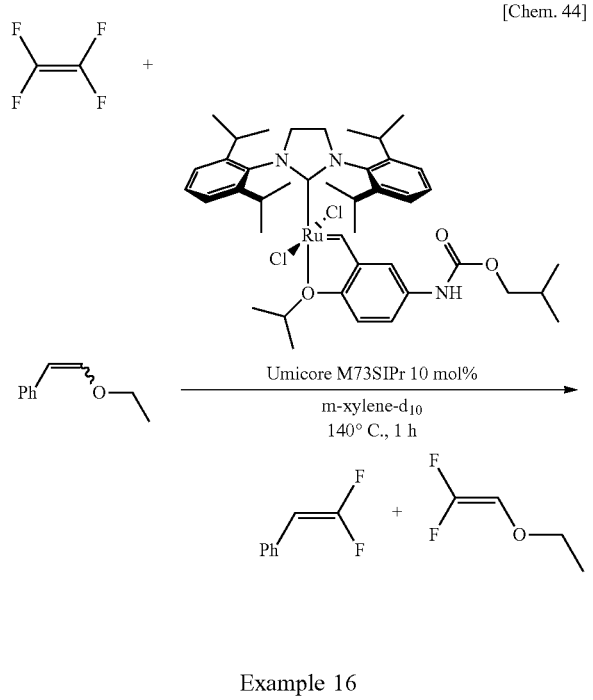

Example 16

Metathesis of Dodecyl Vinyl Ether with Fluorine-Containing Olefin by UmicoreM73SIPr Catalyst In a nitrogen atmosphere, UmicoreM73SIPr catalyst (10 mol %, 0.10 mmol, 82.6 mg), benzene (5.0 mL), and dodecyl vinyl ether (1.0 mmol, 212.4 mg) previously dried with potassium hydroxide were weighed and put in a 100-mL pressure-proof reactor. Cooled in an acetone-dry ice bath, the content liquid was frozen, and the internal pressure was reduced to about 1 mmHg. Subsequently, at room temperature, fluorine-containing olefin (2.0 atm, 10 mmol) was introduced thereinto.

The reactor was heated at 60° C. and the reaction was conducted at the temperature for 1 hour. After the completion of the reaction, p-bis(trifluoromethyl)benzene (internal standard, 1.0 mmol, 214.1 mg) was added to the resultant crude product, and then 0.1 mL thereof was taken out. The taken-out solution was diluted with benzene-$d_6$, and NMR was measured to confirm the reaction proceeding.

The series of reaction is shown below.

The structures 16A to 16D of the fluorine-containing olefins used as the starting material, and the yield of the reaction products and the catalyst turnover number (catalyst turnover frequency per hour), as calculated from the $^{19}$F-NMR spectra thereof, are shown in Table 2.

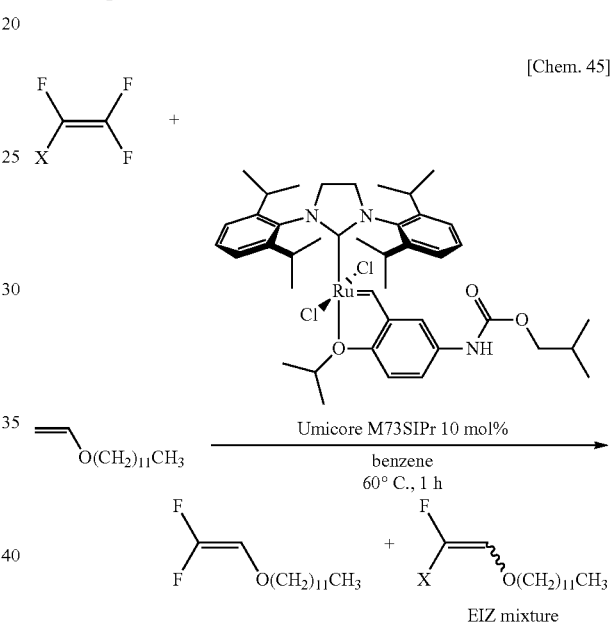

TABLE 2

| | | Product Yield/% | | |
|---|---|---|---|---|
| Ex. | Fluorine-Containing Olefin | ![F2C=CF-O(CH2)11CH3] F O(CH2)11CH3 | ![X,F-C=CF-O(CH2)11CH3] X O(CH2)11CH3 E/Z mixture | Catalyst Turnover Freq. |
| 16A | ![CF2=CF2] | 53 | | 5.3 |
| 16B | ![CF2=CFCl] | 7 | 36 (X=Cl) | 4.3 |

TABLE 2-continued

| Ex. | Fluorine-Containing Olefin | 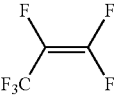 O(CH₂)₁₁CH₃ | 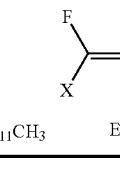 E/Z mixture | Catalyst Turnover Freq. |
|---|---|---|---|---|
| 16C | 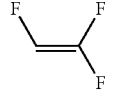 | 0 | 24 (X=CF3) | 2.4 |
| 16D |  | 0 | 59 (X=H) | 5.9 |

The evaluation results of the resultant reaction products ($^{19}$F-NMR (benzene-d$_6$, 283 MHz, trichlorofluoromethane): δ (ppm)) are shown below.

[16A] (2,2-difluorovinyl) dodecyl ether: the same as in Example 14.

[16B] (2-chloro-2-fluorovinyl) dodecyl ether (E/Z isomers)
  Minor isomer: −107.4 (1F, d, J=18 Hz).
  Major isomer: −128.3 (1F, s).

[16C] (2,3,3,3-tetrafluoro-1-propenyl) dodecyl ether (E/Z isomers)
  Minor isomer: −67.6 (3F, d, J=12 Hz), −181.7 (1F, dq, J=9 Hz, 12 Hz).
  Major isomer: −70.3 (3F, d, J=16 Hz), −165.4 (1F, dq, J=19 Hz, 16 Hz).

[16D] (2-fluorovinyl) dodecyl ether (E/Z isomers)
  Minor isomer: −186.6 (1F, dd, J=81 Hz, 8 Hz).
  Major isomer: −162.9 (1F, dd, J=76 Hz, 27 Hz).

Comparative Example 1

Metathesis of Butyl Vinyl Ether with Vinylidene Fluoride by UmicoreM73SIPr Catalyst In a nitrogen atmosphere, UmicoreM73SIPr catalyst (10 mol %, 0.006 mmol), butyl vinyl ether (0.06 mmol—this was previously degassed by freeze-pump-thaw cycles and dried with Molecular Sieve 4A), and benzene-d$_6$ (0.6 mL) with p-bis(trifluoromethyl)benzene (internal standard, 0.02 mmol) dissolved therein were weighed and put in an NMR tube. Subsequently, the vapor phase part in the NMR tube was substituted with vinylidene fluoride (1.0 atm, 2.7 mL, 0.12 mmol).

The NMR tube was heated at 60° C., and the reaction was conducted at the temperature for 1 hour. After the completion of the reaction, NMR and GC-MS of the content liquid were measured, however, formation of butyl (2,2-difluorovinyl) ether was not detected.

The series of reaction is shown below.

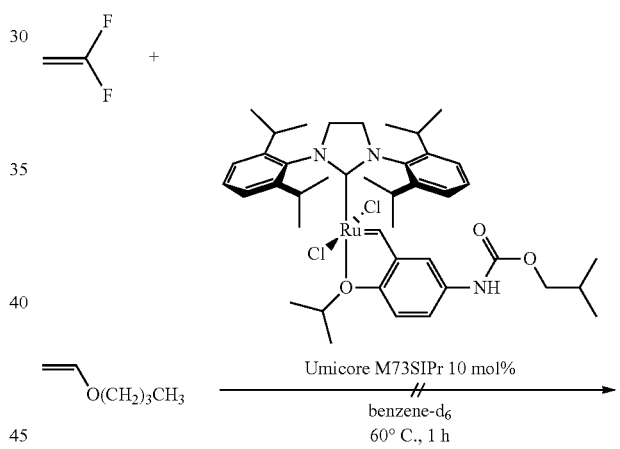

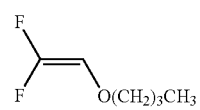

Reference Example 1

Metathesis of (1,3-dimesityl-4,5-dihydroimidazol-2-ylidene)(tricyclohexylphosphine)benzylidene ruthenium dichloride with tetrachloroethylene In a nitrogen atmosphere, tetrachloroethylene (16.6 mg, 0.1 mmol) which was previously degassed by freeze-pump-thaw cycles and dried with Molecular Sieve 4A, (1,3-dimesityl-4,5-dihydroimidazol-2-ylidene)(tricyclohexylphosphine)benzylidene ruthenium dichloride (10 mol %, 0.01 mmol, 8.5 mg), and m-xylene-d$_{10}$ (0.6 mL) were put in an NMR tube. After uniformly mixed, this was heated at 60° C. for 1 hour. Subsequently, this was further heated at 100° C. for 1 hour and at 140° C. for 1 hour in that order. The reaction proceeding was traced through NMR measurement, but only the decomposition of the catalyst was observed while the heating temperature rose. From this, it is concluded that under this reaction condition, olefin metathesis of tetrachloroethylene could not go on.

The series of reactions is shown below.

(1)

(3)

[Chem. 47]

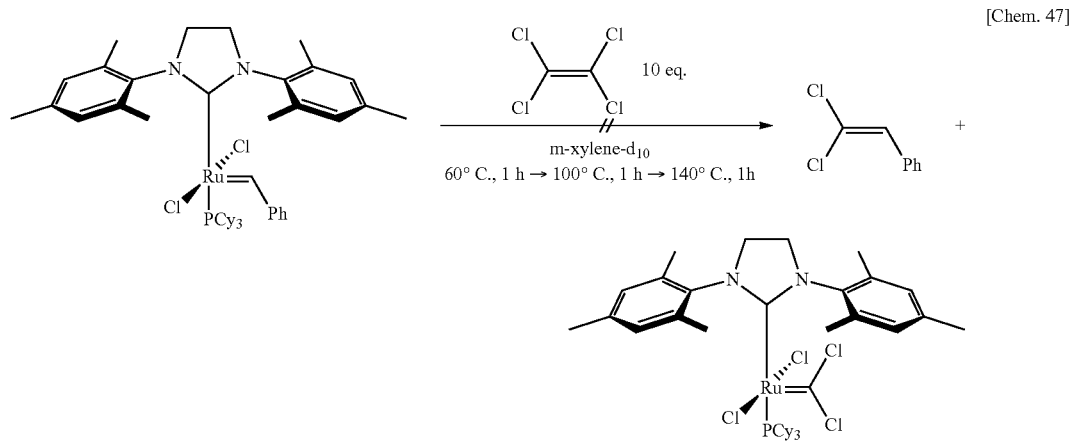

While the present invention has been described in detail and with reference to specific embodiments thereof, it will be apparent to one skilled in the art that various changes and modifications can be made therein without departing from the spirit and scope thereof. The present application is based on a Japanese patent application filed Sep. 6, 2013 (Application No. 2013-185307) and a Japanese patent application filed Jun. 18, 2014 (Application No. 2014-125625), the contents of which are herein incorporated by reference.

INDUSTRIAL APPLICABILITY

According to the present invention, other fluorine-containing olefins such as 1,1-difluoro-2-substituted olefins and the like can be produced simply and efficiently from industrially-easily-available fluorine-containing olefins such as tetrafluoroethylene and the like, through olefin metathesis.

The invention claimed is:

1. A method comprising:
   reacting a compound of formula (2) with a compound of formula (7), in the presence of at least one compound selected from the group consisting of a compound of formula (1), a compound of formula (3), a compound of formula (4), a compound of formula (8), and a compound of formula (9) to produce at least one compound selected from the group consisting of a compound of formula (10), a compound of formula (11), a compound of formula (12), and a compound of formula (13):

-continued

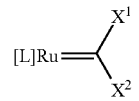

(4)

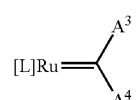

(8)

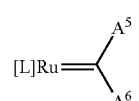

(9)

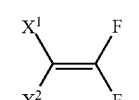

(2)

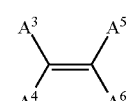

(7)

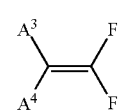

(10)

-continued

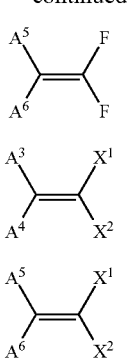

wherein:
[L] is a ligand;
A$^1$ to A$^6$ each independently is a functional group selected from the group consisting of functional group (i), functional group (ii), functional group (iii), and functional group (iv), A$^1$ and A$^2$ may bond to each other to form a ring, A$^3$ and A$^4$ may bond to each other to form a ring, A$^5$ and A$^6$ may bond to each other to form a ring, in the case where one of A$^1$ and A$^2$ is a halogen atom, the other is a functional group selected from the group consisting of the functional group (i), the functional group (iii) and the functional group (iv), in the case where one of A$^3$ and A$^4$ is a halogen atom, the other is a functional group selected from the group consisting of the functional group (i), the functional group (iii) and the functional group (iv), and in the case where one of A$^5$ and A$^6$ is a halogen atom, the other is a functional group selected from the group consisting of the functional group (i), the functional group (iii) and the functional group (iv);
X$^1$ is a fluorine atom, and
X$^2$ each independently is a functional group selected from the group consisting of the functional group (i), the functional group (ii), the functional group (v) and the functional group (vi), provided that:
the functional group (i) is a hydrogen atom;
the functional group (ii) is a halogen atom;
the functional group (iii) is a monovalent hydrocarbon group having a carbon number of from 1 to 20;
the functional group (iv) is a monovalent hydrocarbon group having a carbon number of from 1 to 20 and comprising one or more atoms selected from the group consisting of a halogen atom, an oxygen atom, a nitrogen atom, a sulfur atom, a phosphorus atom, and a silicon atom;
the functional group (v) is a functional group selected from the group consisting of an alkyl group having a carbon number of from 1 to 12, an alkoxy group having a carbon number of from 1 to 12, an aryl group having a carbon number of from 5 to 20, an aryloxy group having a carbon number of from 5 to 20, a (per)halogenated alkyl group having a carbon number of from 1 to 12, a (per)halogenated alkoxy group having a carbon number of from 1 to 12, a (per)halogenated aryl group having a carbon number of from 5 to 20, and a (per)halogenated aryloxy group having a carbon number of from 5 to 20; and
the functional group (vi) is the functional group (v) comprising one or more atoms selected from the group consisting of an oxygen atom, a nitrogen atom, a sulfur atom, a phosphorus atom, and a silicon atom.

2. The method according to claim 1, wherein the compound of the formula (1) is a ruthenium-carbene complex.

3. The method according to claim 1, wherein one of A$^1$ and A$^2$ is a hydrogen atom, and the other is a functional group selected from the group consisting of the functional group (iii) and the functional group (iv).

4. The method according to claim 1, wherein the compound of the formula (3) and the compound of the formula (4) are reaction products of the compound of the formula (1) with the compound of the formula (2).

5. The method according to claim 1, wherein the compound of the formula (8) and the compound of the formula (9) are reaction products of the compound of the formula (3) or the compound of the formula (4) with the compound of the formula (7).

6. The method according to claim 1, wherein, in the formula (2), X$^2$ is a hydrogen atom, a fluorine atom, a chlorine atom, or a trifluoromethyl group.

7. The method according to claim 6, wherein the compound of the formula (2) is tetrafluoroethylene.

8. The method according to claim 1, wherein the compound the formula (7) is at least one compound selected from the group consisting of ethylene, a monosubstituted olefin and a 1,2-disubstituted olefin.

9. The method according to claim 1, wherein the compound of formula (7) is at least one compound selected from the group consisting of a monosubstituted olefin and a 1,2-disubstituted olefin selected from the group consisting of the functional group (iii) and the functional group (iv).

10. The method according to claim 1, wherein the compound of the formula (7) is a compound comprising a hetero atom at the vinyl position thereof.

11. The method according to claim 1, comprising bringing the compound of the formula (1) into contact with the compound of the formula (2) to thereby convert into at least one of the compound of the formula (3) and the compound of the formula (4), and then bringing the converted compound into contact with the compound of the formula (7).

12. The method according to claim 1, comprising bringing at least one of the compound of the formula (3) and the compound of the formula (4) into contact with the compound of the formula (7) to thereby convert into at least one of the compound of the formula (8) and the compound of the formula (9), and then bringing the converted compound into contact with the compound of the formula (2).

13. The method according to claim 1, comprising bringing at least one of the compound of the formula (8) and the compound of the formula (9) into contact with the compound of the formula (2) to thereby convert into at least one of the compound of the formula (3) and the compound of the formula (4), and then bringing the converted compound into contact with the compound of the formula (7).

14. The method according to claim 1, wherein the compound of the formula (2) and the compound of the formula (7) are brought into contact with the compound of the formula (1) simultaneously.

15. The method according to claim 1, wherein the reaction of the compound of formula (2) with the compound of formula (7) forms a 1,1-difluoro-2-substituted olefin.

16. The method according to claim 1, wherein the reacting is carried out in a solvent.

17. The method according to claim 1, wherein at least one of A$^3$, A$^4$, A$^5$, and A$^6$ is an alkoxy group.

18. The method according to claim 1, wherein at least one of A$^3$ and A$^4$ is of formula —O(CH$_2$)$_3$CH$_3$.

19. The method according to claim 1, wherein the compound of formula (7) is an alkyl vinyl ether.

20. The method according to claim 1, wherein the compound of formula (7) is β-alkoxy styrene.

21. The method according to claim 1, wherein the compound of formula (7) is an alkyl vinyl ether having an alkyl group with from 4 to 12 carbon atoms.

22. The method according to claim 1, wherein the compound of formula (2) is at least one selected from the group consisting of tetrafluoroethylene, chlorotrifluoroethylene, hexafluoropropylene and trifluoroethylene.

23. The method according to claim 1, wherein the compound of formula (2) is at least one of:

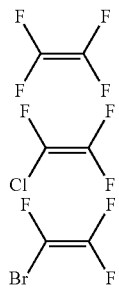

-continued

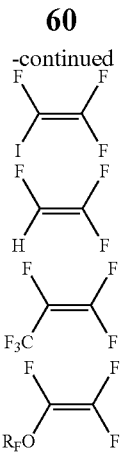

wherein ORF is a (per)halogenated alkoxy group having a carbon number of from 1 to 12, or a (per)halogenated alkoxy group having a carbon number of from 1 to 12 and having an etheric oxygen atom between the carbon atom and the carbon atom.

* * * * *